United States Patent
Kosuge et al.

(10) Patent No.: US 9,515,270 B2
(45) Date of Patent: Dec. 6, 2016

(54) INDOLOPHENOXAZINE COMPOUND AND ORGANIC LIGHT EMITTING DEVICE USING THE SAME

(75) Inventors: Tetsuya Kosuge, Yokohama (JP); Jun Kamatani, Tokyo (JP); Shigemoto Abe, Yokohama (JP); Kengo Kishino, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 710 days.

(21) Appl. No.: 13/885,883

(22) PCT Filed: Nov. 25, 2011

(86) PCT No.: PCT/JP2011/077872
§ 371 (c)(1),
(2), (4) Date: May 16, 2013

(87) PCT Pub. No.: WO2012/077582
PCT Pub. Date: Jun. 14, 2012

(65) Prior Publication Data
US 2013/0228770 A1    Sep. 5, 2013

(30) Foreign Application Priority Data
Dec. 10, 2010   (JP) .................................. 2010-275736

(51) Int. Cl.
| | | |
|---|---|---|
| H01L 51/54 | (2006.01) | |
| C09K 11/06 | (2006.01) | |
| H01L 51/00 | (2006.01) | |
| C07D 471/06 | (2006.01) | |
| C07D 498/06 | (2006.01) | |
| C07D 519/00 | (2006.01) | |
| H01L 51/50 | (2006.01) | |

(52) U.S. Cl.
CPC ......... *H01L 51/0071* (2013.01); *C07D 471/06* (2013.01); *C07D 498/06* (2013.01); *C07D 519/00* (2013.01); *H01L 51/5004* (2013.01); *H01L 51/5016* (2013.01); *H01L 51/5056* (2013.01); *H01L 2251/552* (2013.01)

(58) Field of Classification Search
None
See application file for complete search history.

(56) References Cited

U.S. PATENT DOCUMENTS

| | | |
|---|---|---|
| 7,883,786 B2 | 2/2011 | Abe et al. |
| 7,923,129 B2 | 4/2011 | Igawa et al. |
| 8,110,824 B2 | 2/2012 | Yamada et al. |
| 8,293,383 B2 | 10/2012 | Horiuchi et al. |
| 2011/0024737 A1 | 2/2011 | Horiuchi et al. |
| 2012/0292576 A1* | 11/2012 | Parham ................ C07D 209/86 252/500 |

FOREIGN PATENT DOCUMENTS

| | | | | |
|---|---|---|---|---|
| DE | WO 2011088877 A1 * | 7/2011 | ........... | C07D 209/86 |
| WO | 2010/050778 A1 | 5/2010 | | |

OTHER PUBLICATIONS

U.S. Appl. No. 13/885,124, filed May 13, 2013.

* cited by examiner

*Primary Examiner* — Andrew K Bohaty
(74) *Attorney, Agent, or Firm* — Fitzpatrick, Cella, Harper & Scinto

(57) ABSTRACT

Provided is an organic light emitting device having high emission efficiency and excellent driving durability. The organic light emitting device includes an anode, a cathode, and an organic compound layer disposed between the anode and the cathode, in which the organic compound layer includes an indolophenoxazine compound represented by the following general formula [1]:

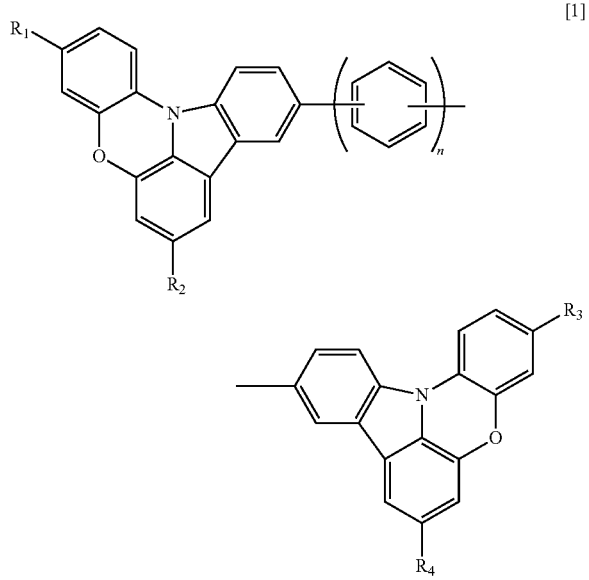

[1]

(in the formula [1], $R_1$ to $R_4$ each represents one of a hydrogen atom and an alkyl group having 1 to 4 carbon atoms, and n represents an integer of 0 to 3).

17 Claims, 1 Drawing Sheet

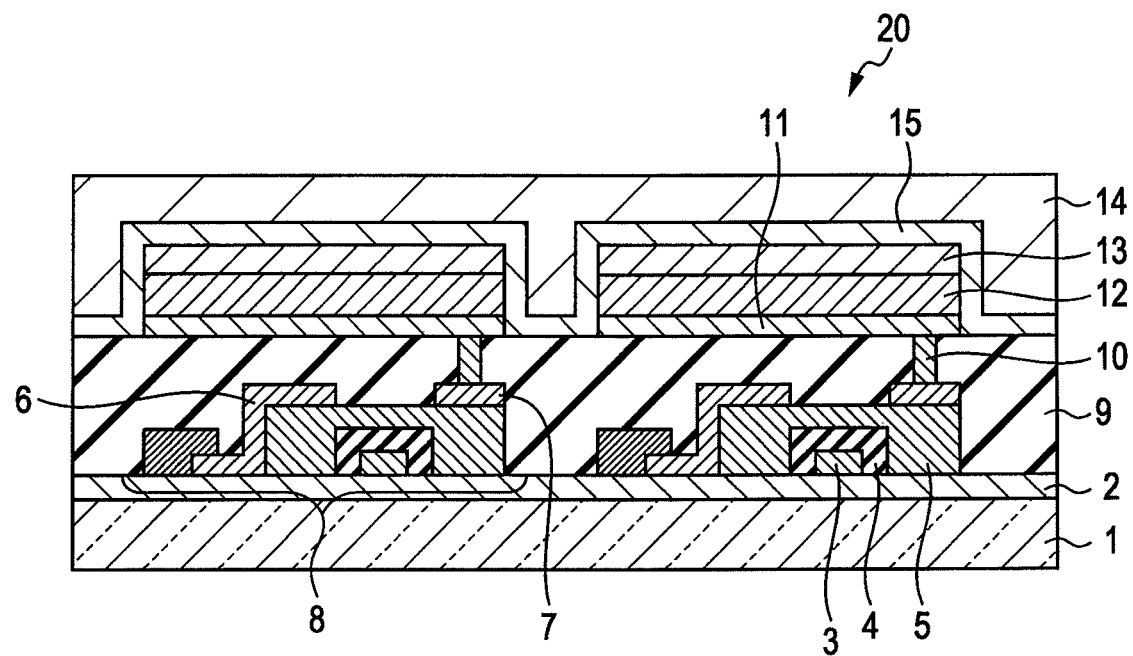

INDOLOPHENOXAZINE COMPOUND AND ORGANIC LIGHT EMITTING DEVICE USING THE SAME

TECHNICAL FIELD

The present invention relates to an indolophenoxazine compound and an organic light emitting device using the same.

BACKGROUND ART

An organic light emitting device is an electronic device including an anode, a cathode, and an organic compound layer disposed between both the electrodes. Holes and electrons to be injected from the respective electrodes recombine with each other in the organic compound layer (in particular, light emitting layer). When excitons generated by the recombination return to the ground state, the organic light emitting device emits light.

Recent advances in the organic light emitting device are remarkable, and have resulted in the following features, for example. That is, the organic light emitting device has a low driving voltage, a variety of emission wavelengths, and high-speed responsiveness, and allows a light emitting device to be reduced in thickness and weight.

Meanwhile, the organic light emitting device is broadly classified into a fluorescent light emitting device and a phosphorescent light emitting device depending on the kind of excitons involved in emission. In particular, the phosphorescent light emitting device is an electronic device including a phosphorescent light emitting material in an organic compound layer, specifically a light emitting layer, which constructs the organic light emitting device, in which triplet excitons are involved in emission. Here, the phosphorescent light emitting material is excited to the triplet state through the recombination of holes and electrons, and emits phosphorescent light when returning to the ground state. Thus, the phosphorescent light emitting device is an organic light emitting device which provides emission derived from the triplet excitons.

Further, the phosphorescent light emitting device has attracted attention in recent years because the internal quantum efficiency of the phosphorescent light emitting device is four times as large as the internal quantum efficiency of the fluorescent light emitting device in theory. However, in the phosphorescent light emitting device, there is a room for further improvement in emission efficiency.

Meanwhile, there are various proposals concerning materials to be used in the phosphorescent light emitting device. Here, a material for constructing a hole transport layer included in the phosphorescent light emitting device is exemplified by the following compounds A and B disclosed in PTL 1.

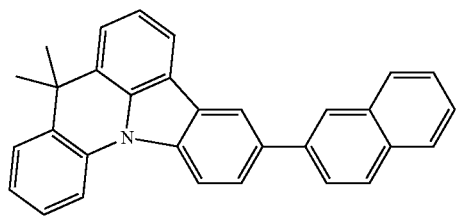

A

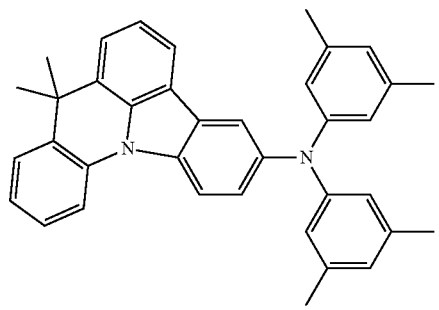

B

CITATION LIST

Patent Literature

PTL 1: International Patent Publication WO2010/050778

SUMMARY OF INVENTION

However, the above-mentioned compound A has a deep HOMO level (large ionization potential). This is because indoloacridine, which serves as a main skeleton in a molecule of the compound, has a deep HOMO level in itself, and besides, there is only one indoloacridine ring in the molecule. On the other hand, the above-mentioned compound B has an indoloacridine ring substituted by an arylamino group, and hence has a shallow HOMO level. However, the arylamine moiety includes a carbon-nitrogen bond capable of rotating freely, and such carbon-nitrogen bond has small bond energy and low chemical stability.

The present invention has been made in order to solve the above-mentioned problems. An object of the present invention is to provide an organic light emitting device having high emission efficiency and excellent driving durability.

An indolophenoxazine compound of the present invention is a compound represented by the following general formula [1]:

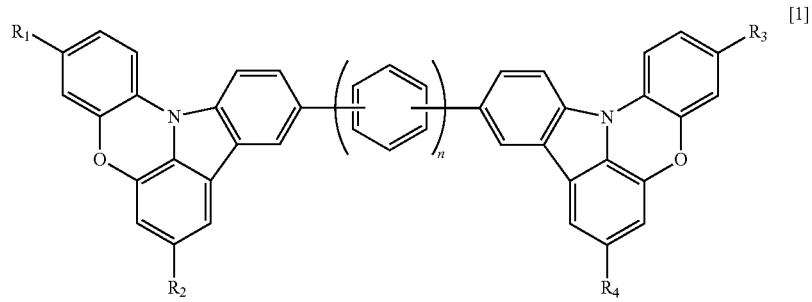

(in the formula [1], $R_1$ to $R_4$ each represents one of a hydrogen atom and an alkyl group having 1 to 4 carbon atoms, and n represents an integer of 0 to 3).

The indolophenoxazine compound of the present invention is a compound having a shallow HOMO level and high chemical stability. Thus, according to the present invention, it is possible to provide the organic light emitting device having high emission efficiency and excellent driving durability.

Further features of the present invention will become apparent from the following description of exemplary embodiments with reference to the attached drawings.

BRIEF DESCRIPTION OF DRAWINGS

FIG. 1 is a cross-sectional schematic diagram illustrating an example of a display apparatus including an organic light emitting device of the present invention and a TFT element as an example of a switching element connected to the organic light emitting device.

DESCRIPTION OF EMBODIMENTS

First, an indolophenoxazine compound of the present invention is described. The indolophenoxazine compound of the present invention is a compound represented by the following general formula [1].

In the formula [1], $R_1$ to $R_4$ each represents one of a hydrogen atom and an alkyl group having 1 to 4 carbon atoms.

Examples of the alkyl group represented by each of $R_1$ to $R_4$ include a methyl group, an ethyl group, an n-propyl group, an iso-propyl group, an n-butyl group, an iso-butyl group, a sec-butyl group, and a tert-butyl group.

It should be noted that the above-mentioned alkyl group may further have a substituent. For example, the alkyl group may further have a substituent such as: a hydrocarbon aromatic ring group such as a phenyl group, a naphthyl group, a phenanthryl group, or a fluorenyl group; a heterocyclic aromatic ring group such as a thienyl group, a pyrrolyl group, or a pyridyl group; a substituted amino group such as a dimethylamino group, a diethylamino group, a dibenzylamino group, a diphenylamino group, a ditolylamino group, or a dianisolylamino group; an alkoxy group such as a methoxy group or an ethoxy group; an aryloxy group such as a phenoxy group or a naphthoxy group; a halogen atom such as fluorine, chlorine, bromine, or iodine; a hydroxy group; a cyano group; or a nitro group.

In the formula [1], n represents an integer of 0 to 3.

In the indolophenoxazine compound of the present invention, it is preferred that all of $R_1$ to $R_4$ in the formula [1] each represent a hydrogen atom. It is more preferred that the indolophenoxazine compound be a compound represented by the following general formula [2].

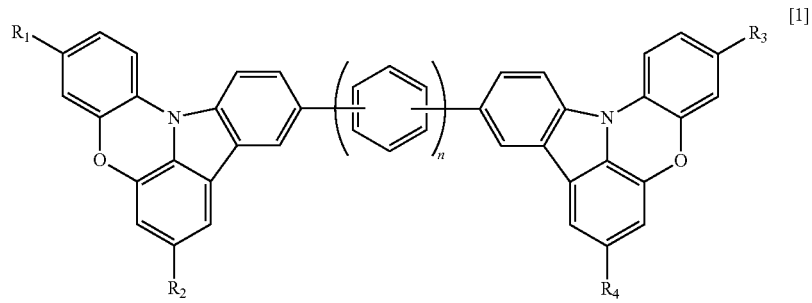

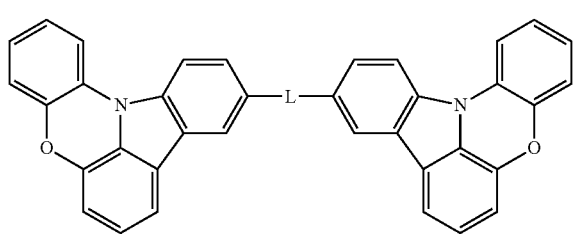

[2]

In the formula [2], L represents one of a single bond, an m-phenylene group, and a p-phenylene group.

Next, a synthesis method for the indolophenoxazine compound of the present invention is described. In the synthesis of the indolophenoxazine compound of the present invention, first, an indolophenoxazine boronic acid ester is synthesized through a synthesis scheme represented by the following formula [3].

[3]

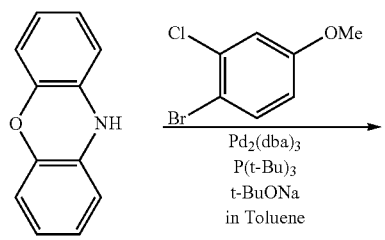

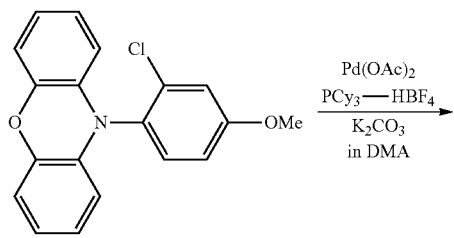

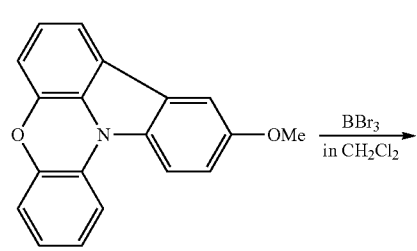

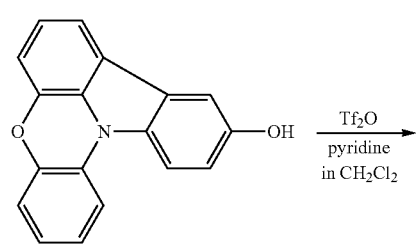

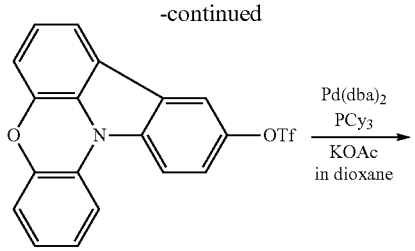

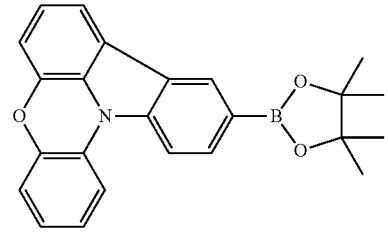

The synthesis scheme of the formula [3] includes the following processes.

(3-1) Coupling of phenoxazine with a dihalogenomethoxybenzene (3-2) Intramolecular cyclization of the compound synthesized in the process (3-1)

(3-3) Process for converting a methoxy group (—OMe→—OH→—OTf→boronic acid ester)

In the above-mentioned processes, indolophenoxazine rings, each of which serves as a main skeleton in the indolophenoxazine compound of the present invention, are formed by the process (3-2). It should be noted that the use of phenoxazine having an alkyl group introduced in advance at a predetermined position (carbon atom at the 3-position and/or 7-position) as a starting material can provide an indolophenoxazine derivative having introduced therein the alkyl group.

An indolophenoxazine boronic acid ester is synthesized according to the synthesis scheme represented by the formula [3]. After that, the indolophenoxazine compound of the present invention is obtained according to a synthesis scheme represented by the following formula [4].

[4]

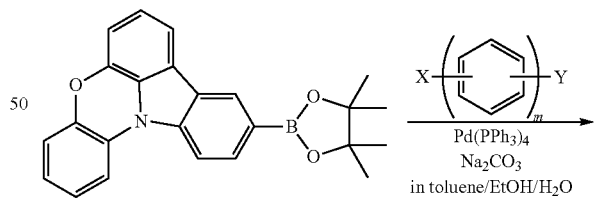

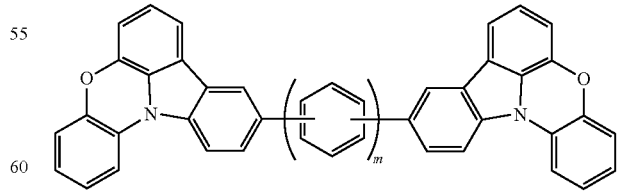

(In the formula [4], X and Y each represents one of chlorine, bromine, and iodine, and m represents an integer of 1 to 3.)

Here, the reaction represented by the formula [4] is a coupling reaction of the indolophenoxazine boronic acid ester (Bpin-substituted indolophenoxazine) obtained according to the synthesis scheme of the formula [3] with a halogenated oligophenylene using a Pd catalyst.

In the synthesis scheme represented by the formula [4], a desired indolophenoxazine compound may be synthesized by appropriately selecting a halogenated oligophenylene. Here, an asymmetric indolophenoxazine compound may also be obtained by appropriately selecting two halogen atoms included in a halogenated oligophenylene. For example, one equivalent each of different kinds of Bpin-substituted indolophenoxazines is allowed to act on a halogenated oligophenylene in which X represents bromine and Y represents chlorine at two stages. As a result, an asymmetric indolophenoxazine compound may be obtained based on a difference in reactivity between coupling reactions with bromine and chlorine.

Meanwhile, when the indolophenoxazine compound of the present invention is used as a material for constructing an organic light emitting device, the compound is preferably subjected to sublimation purification immediately before use. This is because sublimation purification provides a large purification effect in enhancing the purity of an organic compound. In this regard, however, in general, an organic compound having a larger molecular weight needs to be subjected to sublimation purification at a higher temperature. In this case, the organic compound is more liable to undergo heat decomposition and the like due to the higher temperature. Accordingly, it is preferred that the organic compound to be used as a material for constructing an organic light emitting device have a molecular weight of 1,000 or less so that the organic compound may be subjected to sublimation purification without being excessively heated.

As represented by the formula [1], the indolophenoxazine compound of the present invention has a specific basic structure in which two indolophenoxazine rings are included as a main skeleton and the indolophenoxazine rings are linked together via a single bond or an oligophenylene group.

Here, the main skeleton in a compound is a central partial structure in a molecule of the compound. In addition, the main skeleton is also a partial structure which mainly determines physical property values such as lowest singlet excited state energy ($S_1$ energy), lowest triplet excited state energy ($T_1$ energy), an HOMO level, and an LUMO level of the whole compound. Here, in a compound, when a basic structure (main skeleton) having a specified usage such as the number of main skeletons or a bonding position in a molecule of the compound is determined, compounds each having the basic structure have almost the same physical properties and can commonly have physical properties which strongly reflect features of the main skeleton.

On the other hand, a subsidiary skeleton for the main skeleton is an auxiliary partial structure in a molecule of a compound, does not have any large influence on physical properties of the whole compound, and is used for the fine adjustment of the physical properties. In the indolophenoxazine compound of the present invention, the substituents $R_1$ to $R_4$ shown in the formula [1] and the oligophenylene group each correspond to the subsidiary skeleton.

Meanwhile, indolophenoxazine, which serves as a main skeleton, has the following features.

Indolophenoxazine has a structure in which a benzene ring and a carbazole ring each constructing 9-phenylcarbazole are further cross-linked together via one ether bond (—O—). It is generally said that, in 9-phenylcarbazole shown below, a carbon-nitrogen bond (hereinafter, referred to as carbazole type C—N bond) connecting a benzene ring to a carbazole ring has small bond energy and has low chemical stability. That is, during the excitation of 9-phenylcarbazole, the carbazole type C—N bond is liable to be cleaved. Further, once the carbazole type C—N bond is cleaved, a phenyl group dissociates from a carbazolyl group in a system, which makes it difficult to maintain a 9-phenylcarbazole structure. This is because the carbazole type C—N bond is liable to undergo radical cleavage caused by excitation energy. When a compound having such weak bond is used as a material for constructing an organic compound layer in an organic light emitting device, the compound is liable to deteriorate during driving the device, resulting in a reduction in driving durability of the device. Similarly, it can be said that a carbon-nitrogen bond in an arylamine structure (hereinafter, referred to as arylamine type C—N bond) shown below also has small bond energy and low chemical stability.

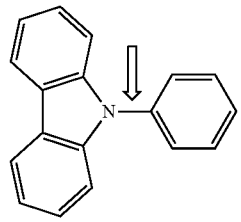 [SMILES: c1ccc(-n2c3ccccc3c3ccccc32)cc1]

Carbazole type C—N bond

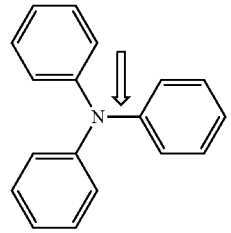

Arylamine type C—N bond

In contrast, the indolophenoxazine compound of the present invention has high chemical stability as a whole because the carbazole type C—N bond is reinforced by cross-linking the carbazole ring and the benzene ring together via an ether bond. That is, even when the carbazole type C—N bond included in the indolophenoxazine skeleton is cleaved, the benzene ring and the carbazole ring are still cross-linked together via an ether bond. Thus, even after the cleavage of the carbazole type C—N bond, the benzene ring and the carbazole ring are present adjacent to each other. Therefore, the carbazole type C—N bond is more likely to be regenerated through the recombination of the benzene ring and the carbazole ring, and hence the compound itself is hard to deteriorate. It can therefore be said that the indolophenoxazine compound of the present invention has high chemical stability.

Further, indolophenoxazine has a feature of having a shallower HOMO level than other similar compounds. Table 1 below shows HOMO levels of indolophenoxazine and its similar compounds. It should be noted that the HOMO levels shown in Table 1 are calculated values obtained by molecular orbital calculation.

TABLE 1

| | Structural formula | HOMO level (calculated value) |
|---|---|---|
| Indolophenoxazine | [structure] | −4.98 eV |
| 8,8'-Dimethylindoloacridine | [structure] | −5.18 eV |
| 9-Phenylcarbazole | [structure] | −5.33 eV |

In Table 1, 8,8'-dimethylindoloacridine is in common with indolophenoxazine in that a carbazole ring and a benzene ring each constructing 9-phenylcarbazole are cross-linked together via one covalent bond having electron donating property. In this regard, however, 8,8'-dimethylindoloacridine has the rings cross-linked together via an alkyl group having electron donating property, whereas indolophenoxazine has the rings cross-linked together via an oxygen atom (ether bond) having higher electron donating property. The HOMO level of indolophenoxazine is shallower than that of 8,8'-dimethylindoloacridine based on the difference in electron donating property. In addition, the compound of the present invention having indolophenoxazine as a main skeleton is a compound having a shallow HOMO level based on the main skeleton.

In general, when holes are injected from a hole transport layer toward a light emitting layer in an organic light emitting device, a smaller difference in HOMO level at an interface between the hole transport layer and the light emitting layer leads to a smaller voltage at which the device is driven. On the other hand, when the light emitting layer is formed of a host having a deep HOMO level and a guest having a shallow HOMO level and holes are injected from the hole transport layer having a shallow HOMO level to the light emitting layer, the following is known. That is, even in the case where there is a large difference in HOMO level between a hole transporting material included in the hole transport layer and the host included in the light emitting layer, when the guest is sufficiently doped in the light emitting layer, the holes are directly injected to the guest. There is known, as the guest having a shallow HOMO level as described above, an iridium complex, which serves as a phosphorescent light emitting material. For example, a phosphorescent light emitting material Ir(ppy)$_3$, which emits green light, has an HOMO level of about −5.6 eV. In this case, it is advantageous to use, as a material for constructing a hole transport layer, a material having an HOMO level as shallow as about −5.6 eV because a voltage at which the device is driven can be reduced. Here, the indolophenoxazine compound of the present invention has a shallow HOMO level, and hence is preferably used as a material for constructing a hole transport layer (hole transporting material) in an organic light emitting device in which a phosphorescent light emitting material having a shallow HOMO level is used as a guest for a light emitting layer.

Further, the indolophenoxazine compound of the present invention has a specific basic structure in which two indolophenoxazine rings are linked together via a single bond or an oligophenylene group. By virtue of the basic structure, the indolophenoxazine compound of the present invention includes features described below.

The first of the features possessed by the indolophenoxazine compound of the present invention is a shallow HOMO level. The indolophenoxazine compound of the present invention has a basic structure in which two indolophenoxazine rings, each of which serves as a main skeleton, are present in one molecule. Thus, the HOMO level of the compound itself is shallower than that of a compound having one indolophenoxazine ring. This is because the ratio of an indolophenoxazine skeleton (main skeleton) in the whole compound is high, and hence the property of a shallow HOMO level derived from the indolophenoxazine main skeleton is more highlighted. In this regard, however, a compound having three or more indolophenoxazine rings in a molecule is not preferred because the molecular weight of the compound becomes excessively large, which makes it difficult to perform sublimation purification or vacuum heating vapor deposition.

The second of the features possessed by the indolophenoxazine compound of the present invention is a high hole mobility. This is related to the fact that, in general, in an arylamine-based compound, a diamine structure shows a higher hole mobility than that of a monoamine structure. That is, a bis(indolophenoxazine) structure includes more N atoms than a mono(indolophenoxazine) structure, and hence shows a higher hole mobility.

The third of the features possessed by the indolophenoxazine compound of the present invention is high lowest triplet excited state energy ($T_1$ energy). This is a structural feature based on a basic structure of the indolophenoxazine compound of the present invention in which two indolophenoxazine rings are linked together via a single bond or an oligophenylene group.

In general, in a phosphorescent light emitting device, in order to enhance the emission efficiency of the device, it is necessary to prevent triplet excitons in a light emitting layer from leaking to an adjacent layer such as a hole transport layer and undergoing nonradiative deactivation. For that purpose, the $T_1$ energy of a material used for any adjacent layer other than the light emitting layer is also desirably higher than the $T_1$ energy of a phosphorescent light emitting material. Specifically, in a green phosphorescent light emitting device, the $T_1$ energy of a material for an adjacent layer is desirably 500 nm or less in terms of a wavelength so as to be higher than the $T_1$ energy of a light emitting material. It can therefore be said that a compound having high $T_1$ energy has a large advantage in the phosphorescent light emitting device.

Meanwhile, in general, the $T_1$ energy of an aromatic compound becomes lower as the n-conjugated plane of the compound becomes larger. Table 2 below shows $T_1$ energy values of major aromatic compounds themselves including indolophenoxazine. It should be noted that Table 2 shows the $T_1$ energy values in terms of a wavelength.

TABLE 2

| | Structural formula | $T_1$ energy (in terms of wavelength) |
|---|---|---|
| Benzene | | 339 nm |
| Carbazole | | 407 nm |
| Biphenyl | | 438 nm |
| Phenoxazine | | 456 nm |
| Inolophenoxazine | | 460 nm |
| Naphthalene | | 472 nm |
| Chrysene | | 500 nm |

As seen from Table 2, indolophenoxazine has a large π-conjugated plane but has $T_1$ energy as relatively high as 460 nm. This is because an indolophenoxazine ring is a heteroaromatic ring including a heteroatom other than carbon. When the indolophenoxazine ring is further substituted by an aryl group, the resultant compound has extended π-conjugation and reduced $T_1$ energy. In this case, when the aryl group to be introduced into the indolophenoxazine ring has lower $T_1$ energy than that of the indolophenoxazine ring and is a substituent derived from an aromatic compound in which the compound itself has extended π-conjugation, the $T_1$ energy of the resultant compound itself may lower remarkably. For example, the introduction of naphthalene, chrysene, or the like shown in Table 2 may remarkably reduce the $T_1$ energy of the resultant compound itself.

In view of the foregoing, in the present invention, an oligophenylene group with less extended π-conjugation is used so that a reduction in $T_1$ energy becomes small in the case where two indolophenoxazine rings are linked together via a substituted arylene group. By virtue of such linkage of two indolophenoxazine rings via an oligophenylene group, the $T_1$ energy of the indolophenoxazine compound of the present invention is as relatively high as 500 nm or less in terms of a wavelength. Thus, even when the indolophenoxazine compound of the present invention is used as a material for constructing a green phosphorescent light emitting device, the emission efficiency of the device does not lower. In addition, when the $T_1$ energy of the compound is 460 nm or less, the compound may also be used as a material for constructing a blue phosphorescent light emitting device.

Moreover, even when a single bond is used as a linking group to directly link two indolophenoxazine rings together, a reduction in $T_1$ energy is relatively small, and the $T_1$ energy is as high as that obtained in the case where the rings are linked together via the oligophenylene group. This is because the indolophenoxazine ring, which is a heteroaromatic ring, has high $T_1$ energy in itself as described above.

In addition, the indolophenoxazine compound of the present invention has indolophenoxazine rings each substituted by a linking group at a predetermined position. Here, substitution position numbers of the indolophenoxazine ring are shown below.

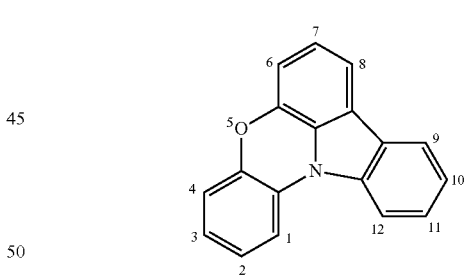

The indolophenoxazine compound of the present invention has indolophenoxazine rings each substituted at the 10-position by a linking group.

Here, out of the eleven substitution positions of the indolophenoxazine ring except the oxygen atom, positions easily subjected to synthesis from the viewpoint of regioselectivity are four positions, i.e., the 3-, 7-, 10-, and 11-positions. Thus, compounds substituted at those positions by a phenyl group were each determined for its $T_1$ energy. Table 3 below shows the results. It should be noted that $T_1$ energy values shown in Table 3 (in terms of a wavelength) are calculated values determined by molecular orbital calculation.

TABLE 3

| Substitution position | 3-Position | 7-Position | 10-Position | 11-Position |
|---|---|---|---|---|
| Structural formula | | | | |
| $T_1$ energy (calculated value) | 453 nm | 439 nm | 428 nm | 439 nm |

As seen from Table 3, when the indolophenoxazine ring is substituted at (the carbon atom at) the 10-position by the phenyl group, the $T_1$ energy becomes highest. It can therefore be said that the indolophenoxazine compound of the present invention having a linking group at the carbon atom at the 10-position of the indolophenoxazine ring has higher $T_1$ energy than that of a compound having a linking group at any other substitution position.

As described above, the indolophenoxazine compound of the present invention represented by the general formula [1] is a compound having two indolophenoxazine rings, each of which serves as a main skeleton, linked together via a single bond or an oligophenylene linking group at the 10-position of each of the indolophenoxazine rings. In addition, by virtue of such specific molecular structure, the indolophenoxazine compound of the present invention has high chemical stability, and the use of the compound as a material for constructing an organic light emitting device provides a device which is hard to undergo material deterioration and has a long life. Further, the indolophenoxazine compound of the present invention has a shallow HOMO level and a high hole transportability. Accordingly, the use of the indolophenoxazine compound of the present invention as a material for constructing a hole transport layer or a hole injection layer (or a hole injection/transport layer) constructing an organic light emitting device facilitates the injection and transport of holes to be injected from an anode. As a result, a balance between carriers in the whole device can be improved to provide an organic light emitting device having high efficiency and a long life. In addition, the indolophenoxazine compound of the present invention has high $T_1$ energy, and hence the use of the compound as a material for constructing a hole transport layer or a hole injection layer (or a hole injection/transport layer) constructing a phosphorescent light emitting device as described above provides an organic light emitting device having high emission efficiency.

Further, in the indolophenoxazine compound of the present invention, as represented by the formula [1], an alkyl group having 1 to 4 carbon atoms may be introduced as a substituent at each of the positions of $R_1$ to $R_4$. Here, when the alkyl group is introduced at each of the positions of $R_1$ to $R_4$, the introduced alkyl group acts as an electron donating group, and the resultant compound has a shallower HOMO level than that of an unsubstituted compound. It should be noted that, when the alkyl group is introduced, the alkyl group acts as a steric hindrance group for reducing an intermolecular interaction, with the result that the resultant compound may have a poorer hole transportability than that of an unsubstituted compound. However, the alkyl group represented by each of the substituents $R_1$ to $R_4$ is merely an auxiliary substituent, does not greatly alter physical properties of the indolophenoxazine compound of the present invention, and is used only for the fine adjustment of the physical properties.

Similarly, as an auxiliary moiety which does not greatly alter physical property values, there is given an oligophenylene group included in the indolophenoxazine compound of the present invention represented by the general formula [1]. The number of benzene rings included in the oligophenylene group (n value) is an integer of 0 to 3. In this regard, however, the physical properties of the indolophenoxazine compound of the present invention are not greatly altered with any n value. That is, the n value is used only for the fine adjustment of the physical properties of the indolophenoxazine compound of the present invention. It should be noted that a larger molecular weight makes it difficult to perform sublimation purification or vacuum heating vapor deposition, and hence the number of phenylene groups (n value) is preferably 0 or 1. Meanwhile, as the phenylene groups each constructing the oligophenylene group, there are given three phenylene groups, i.e., an o-phenylene group, an m-phenylene group, and a p-phenylene group, or combinations thereof. Of those, an m-phenylene group, which shows the smallest reduction in $T_1$ energy, is preferred.

Specific examples of the indolophenoxazine compound of the present invention are shown below. In this regard, however, compounds listed below are merely specific examples, and the present invention is by no means limited thereto.

IP101
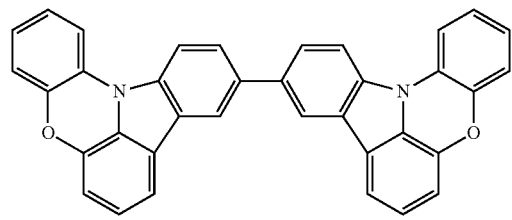
IP102
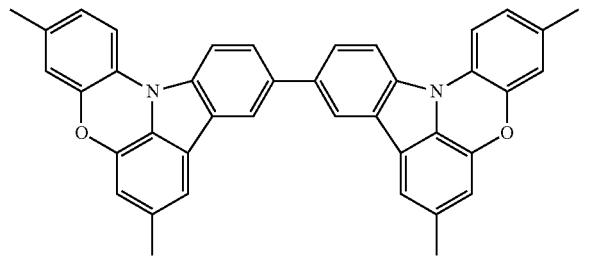
IP103
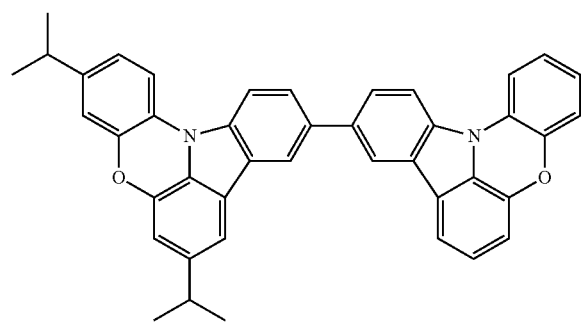
IP104
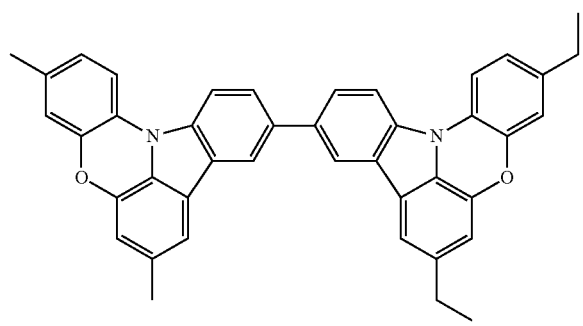
IP105
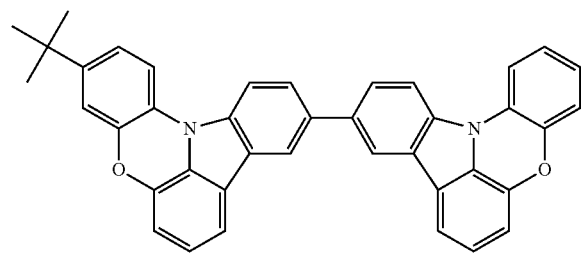
IP106
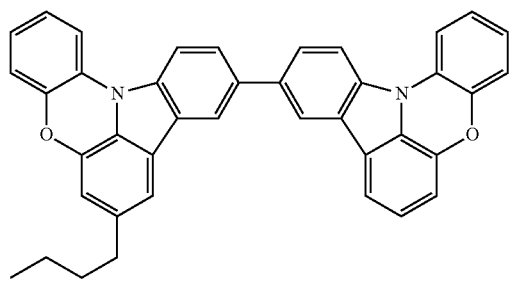
IP201
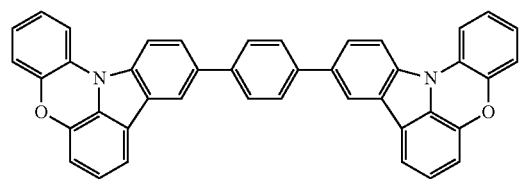
IP202
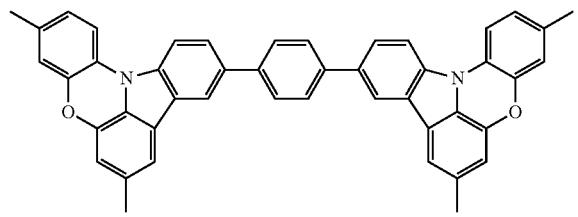
IP203
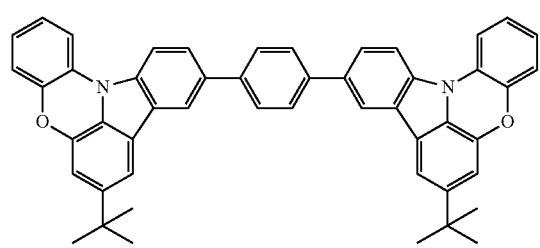
IP204
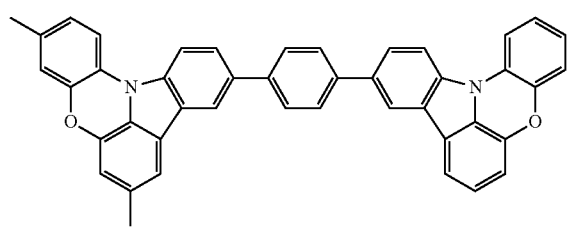

-continued
IP301
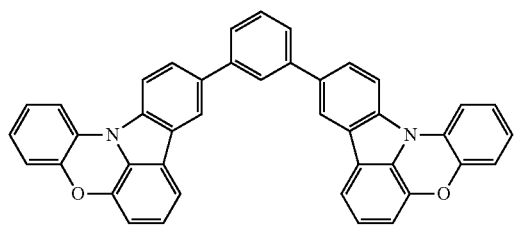
IP302
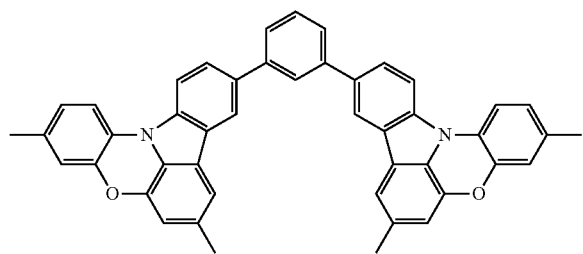
IP303
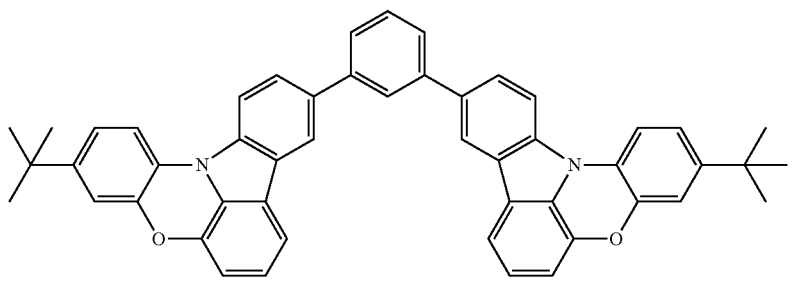
IP304
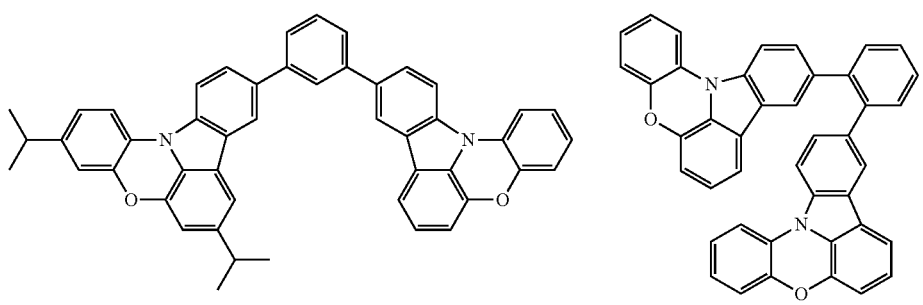
IP401
IP402 IP403
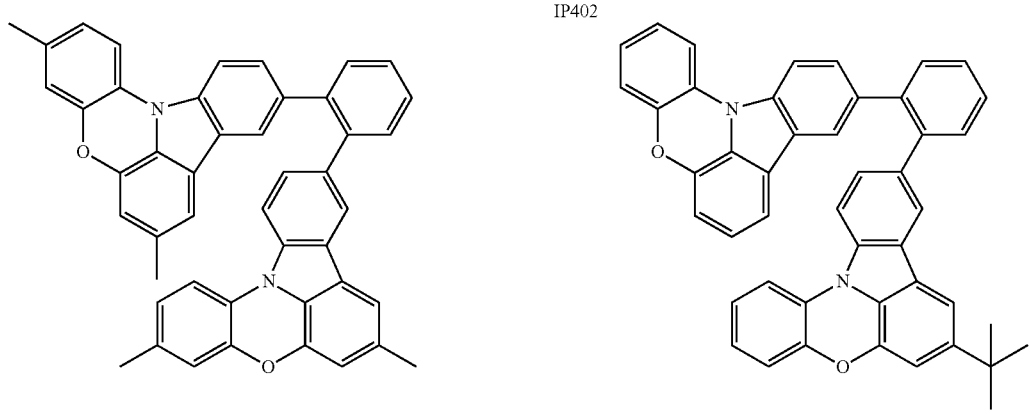
IP501
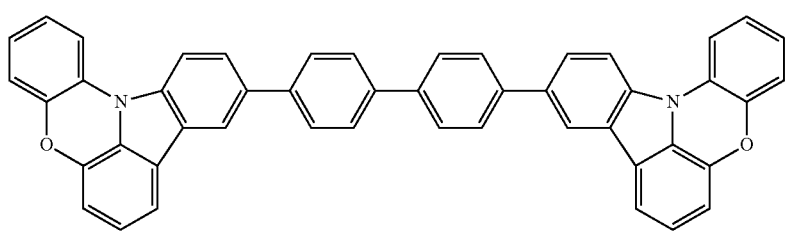

-continued
IP502
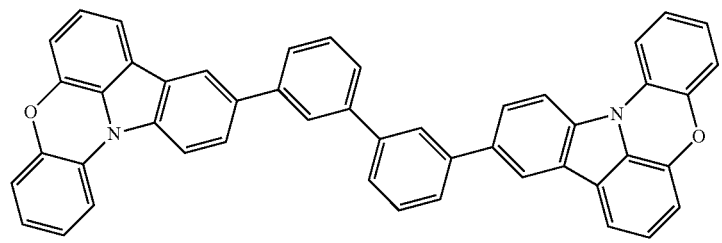
IP503
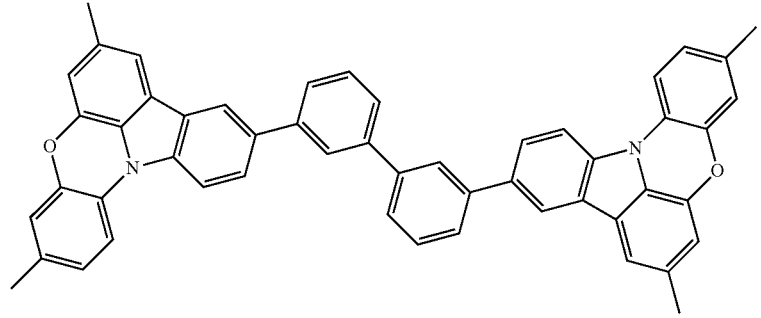
IP504
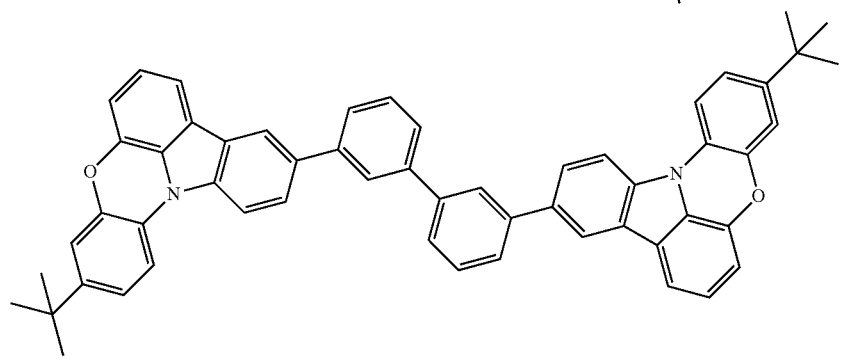
IP505
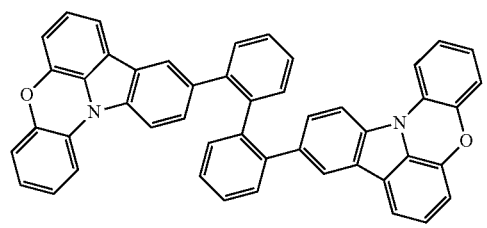
IP506
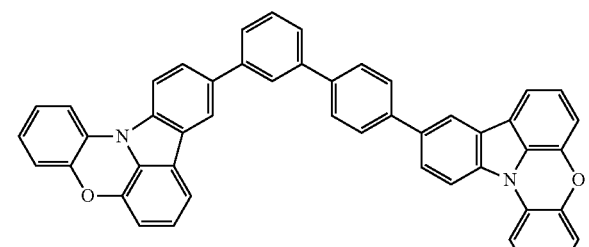
IP507
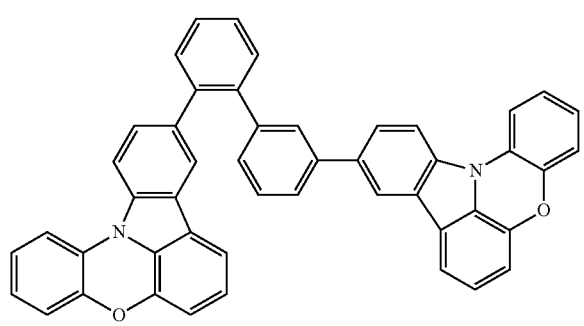
IP508
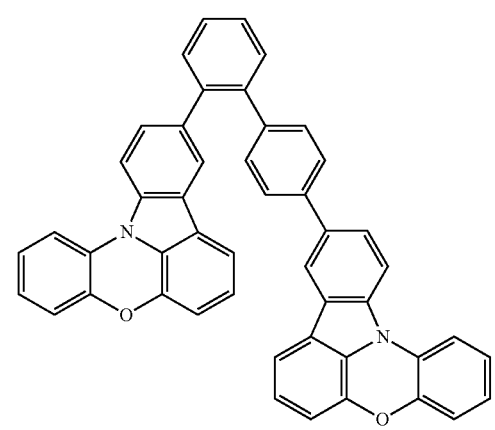

-continued
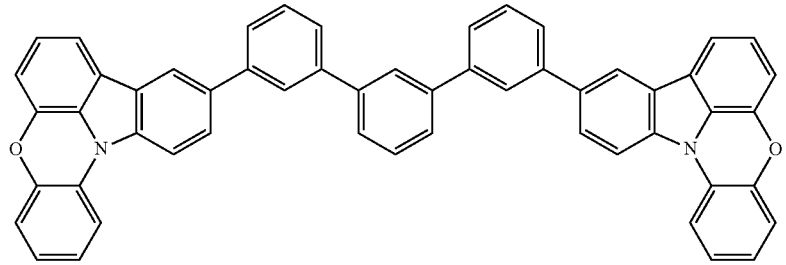
IP601
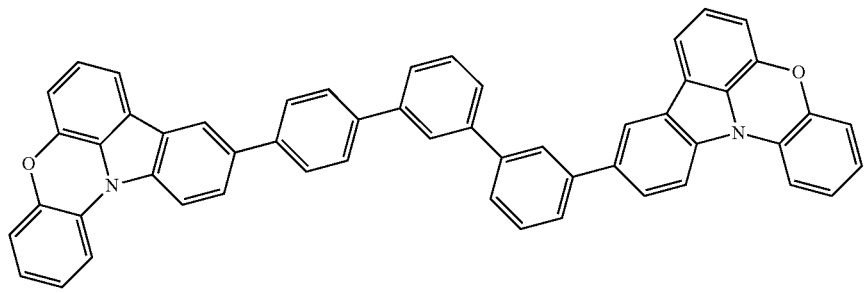
IP602
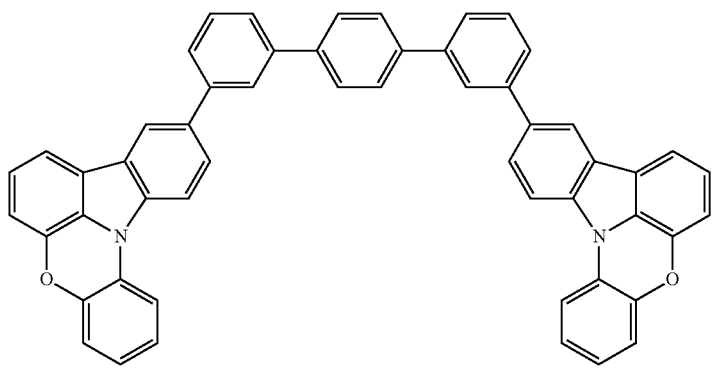
IP603
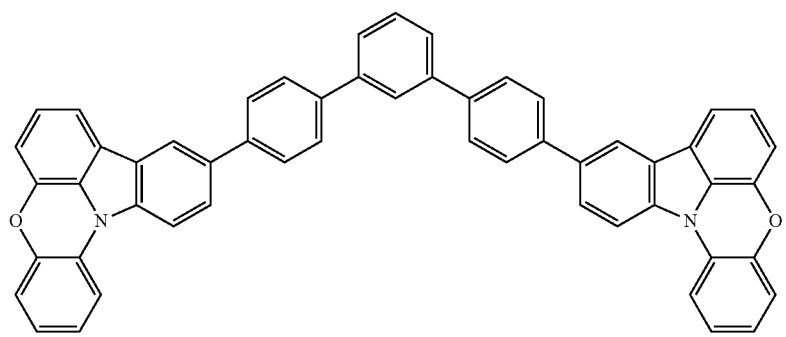
IP604
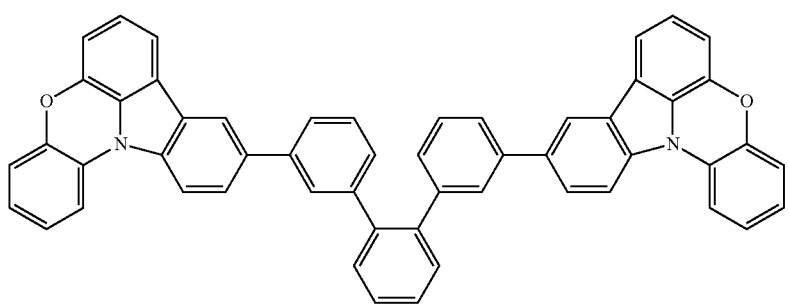
IP605

The compounds belonging to Group n0 out of the above-mentioned exemplified compounds, i.e., IP101 to IP106 are each a compound in which n represents 0 in the formula [1]. The compounds belonging to Group n0 are each characterized by having a shallow HOMO level in particular.

The compounds belonging to Group n1 out of the above-mentioned exemplified compounds, i.e., IP201 to IP204, IP301 to IP304, and IP401 to IP403 are each a compound in which n represents 1 in the formula [1]. Here, in IP201 to IP204, two indolophenoxazine rings are linked together via a p-phenylene group. Further, in IP301 to IP304, two indolophenoxazine rings are linked together via an m-phenylene group. Meanwhile, in IP401 to IP403, two indolophenoxazine rings are linked together via an o-phenylene group. Out of the compounds belonging to Group n1, IP301 to IP304 each have high $T_1$ energy in particular.

The compounds belonging to Group n2 out of the above-mentioned exemplified compounds, i.e., IP501 to IP508 are each a compound in which n represents 2 in the formula [1]. Further, the compounds belonging to Group n3 out of the above-mentioned exemplified compounds, i.e., IP601 to IP605 are each a compound in which n represents 3 in the formula [1]. When n in the formula [1] represents 2 or more in the indolophenoxazine compound of the present invention, the HOMO level and $T_1$ energy of the compound itself can be finely adjusted with an n value and a combination of multiple connection modes (o-, m-, and p-) of phenylene.

Next, the organic light emitting device of the present invention is described.

The organic light emitting device of the present invention is a light emitting device including a pair of electrodes opposite to each other, i.e., an anode and a cathode, and an organic compound layer disposed between the pair of electrodes. Here, the organic compound layer includes a layer including a light emitting material, i.e., light emitting layer. Further, in the organic light emitting device of the present invention, the organic compound layer includes the indolophenoxazine compound of the present invention.

As specific aspects of the organic light emitting device of the present invention, there are given the following aspects.

(i) (Substrate/)anode/light emitting layer/cathode
(ii) (Substrate/)anode/hole transport layer/electron transport layer/cathode
(iii) (Substrate/)anode/hole transport layer/light emitting layer/electron transport layer/cathode
(iv) (Substrate/)anode/hole injection layer/hole transport layer/light emitting layer/electron transport layer/cathode
(v) (Substrate/)anode/hole transport layer/light emitting layer/hole-exciton blocking layer/electron transport layer/cathode Here, a hole injection layer may be called a hole transport layer adjacent to an anode out of multiple hole transport layers as shown in the aspect (iv), for example. Thus, the hole transport layer, which may also be used as the hole injection layer, may be called a hole injection/transport layer.

In this regard, however, the above-mentioned aspects ((i) to (v)) are merely the most basic device constructions, and the present invention is by no means limited thereto. For example, there may be adopted a variety of layer constructions and aspects as described below. That is, an insulating layer, an adhesion layer, or an interference layer may be provided at an interface between each of electrodes and an organic compound layer, or an electron transport layer or a hole transport layer may be constructed of two layers having different ionization potentials.

In the organic light emitting device of the present invention, an embodiment of the device may be the so-called top emission mode involving extracting light from an electrode on the side opposite to the substrate, or may be the so-called bottom emission mode involving extracting light from the substrate side. Alternatively, there may be adopted a construction in which light is extracted from both sides using a substrate and electrodes each formed of a material having light transparency.

In the organic light emitting device of the present invention, the indolophenoxazine compound of the present invention is included in an organic compound layer constructing the device. More specifically, the compound is included in any one of a hole injection layer (hole injection/transport layer), a hole transport layer, a light emitting layer, a hole-exciton blocking layer, an electron transport layer, and an electron injection layer. It is preferred that the compound be included in the hole injection layer (hole injection/transport layer) or the hole transport layer.

In this case, the light emitting layer may be constructed of multiple kinds of components, and the components may be classified into a main component and a subsidiary component. Here, the main component refers to a compound having the maximum weight ratio out of all compounds for constructing the light emitting layer, and may be called a host. On the other hand, the subsidiary component refers to a compound other than the main component, and may be called a guest (dopant), an emission assisting material, a charge injecting material, or the like depending on the function thereof. Here, the guest refers to a compound which is responsible for main emission in the light emitting layer. On the other hand, the host refers to a compound which is present as a matrix around the guest in the light emitting layer, and is a compound which is mainly responsible for the transport of carriers and the donation of excitation energy to the guest.

The concentration of the guest with respect to the host is 0.01 wt % or more to 50 wt % or less, preferably 0.1 wt % or more to 20 wt % or less, more preferably 0.1 wt % or more to 10 wt % or less based on the total amount of materials for constructing the light emitting layer. In particular, the concentration of the guest is desirably 10 wt % or less from the viewpoint of preventing concentration quenching. Further, the guest may be uniformly included in the whole layer formed of the host or may be included with a concentration gradient, or a region free of the guest may be provided in a host layer by partially incorporating the guest in a specific region.

It is preferred that the indolophenoxazine compound of the present invention be used as a hole injecting/transporting material included in a hole injection layer (hole injection/transport layer) or a hole transport layer. It is more preferred that the compound be used as a hole injecting/transporting material included in a phosphorescent light emitting device in which a phosphorescent light emitting material is used as a guest. In this case, the emission color of the phosphorescent light emitting material is not particularly limited, but a green light emitting material having a maximum emission peak wavelength within the range of 500 nm or more to 530 nm or less is preferred.

When the indolophenoxazine compound of the present invention is used as a hole injecting/transporting material included in a phosphorescent light emitting device, a phosphorescent light emitting material to be used as a guest for a light emitting layer is a metal complex. Specifically, there are given an iridium complex, a platinum complex, a rhenium complex, a copper complex, a europium complex, and a ruthenium complex. Of those, an iridium complex, which has strong phosphorescent property, is preferred. Further, multiple phosphorescent light emitting materials may be incorporated into the light emitting layer for the purpose of assisting the transmission of excitons and carriers.

Specific examples of the iridium complex as the phosphorescent light emitting material to be used as the material for constructing the organic light emitting device of the present invention are shown below. In this regard, however, the present invention is by no means limited thereto.

Ir-1

Ir-2

Ir-3

Ir-4

Ir-5 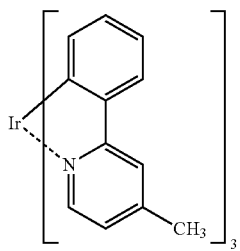

Ir-6 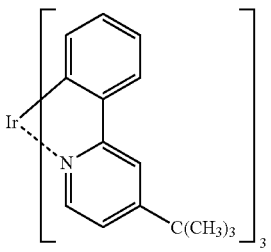

Ir-7

Ir-8 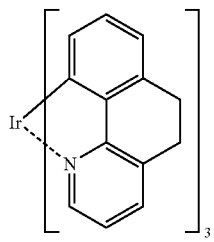

Ir-9 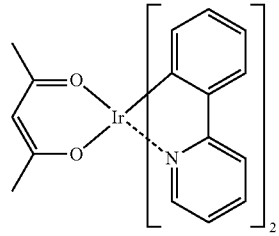

Ir-10 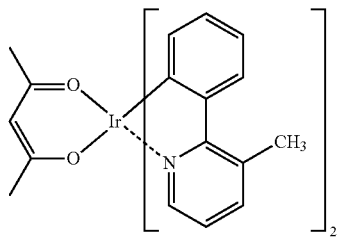

Ir-11 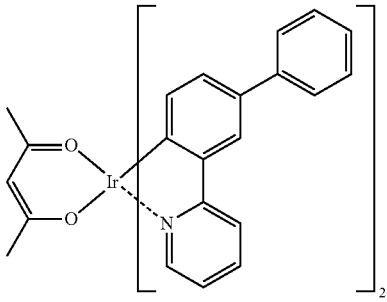 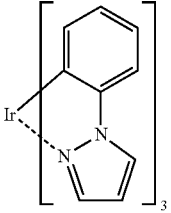

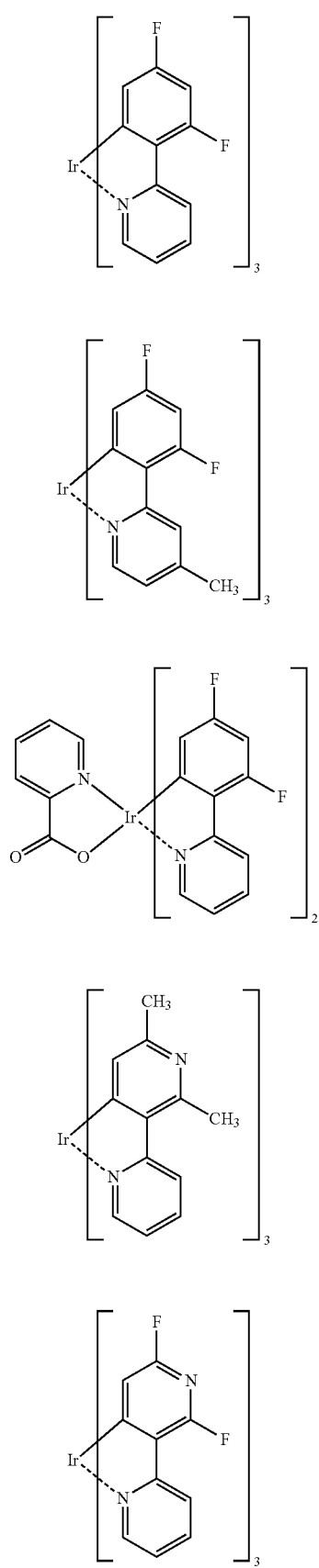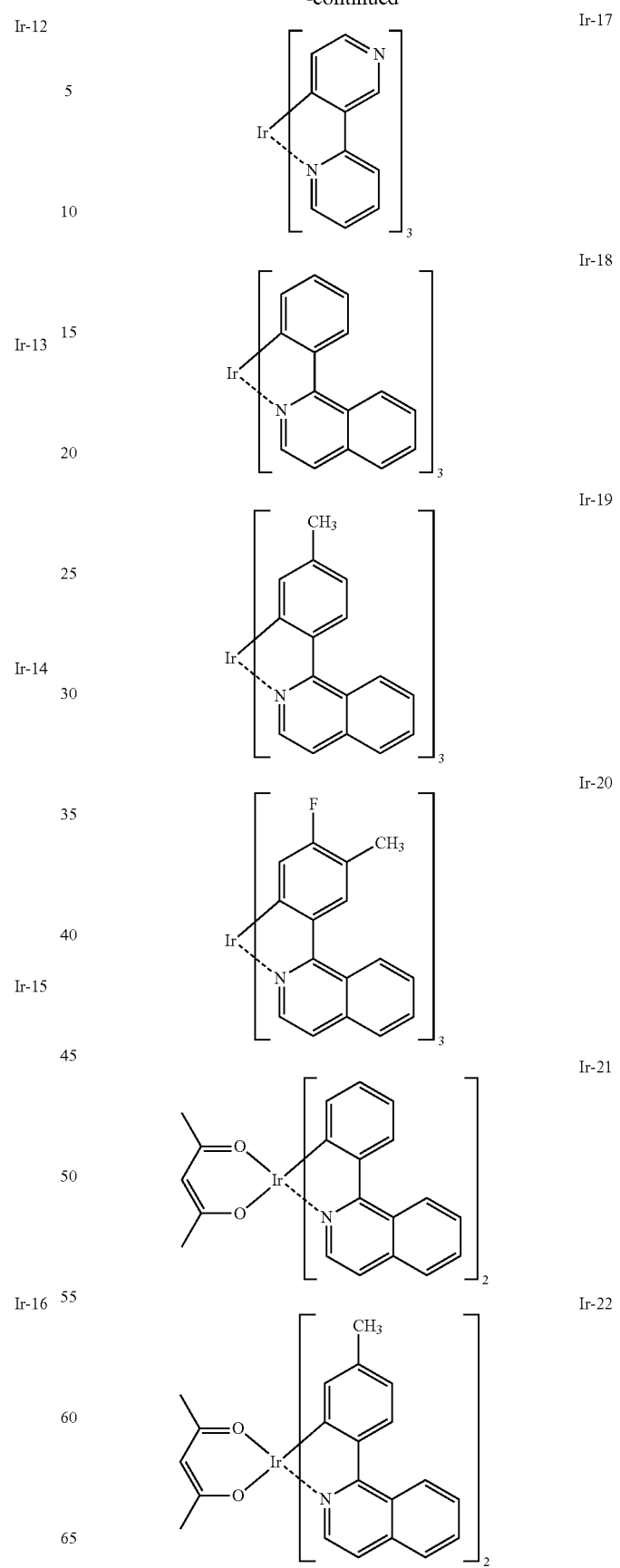

-continued

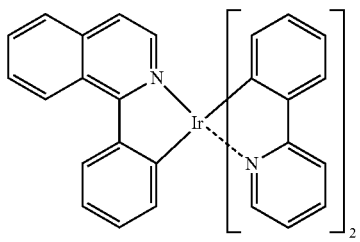

Ir-23

Here, a conventionally known low-molecular or high-molecular compound may be used, as necessary, in addition to the indolophenoxazine compound of the present invention. More specifically, the compound of the present invention may be used in combination with a hole injecting/transporting material, a host included in a light emitting layer, a light emitting compound, an electron injecting/transporting material, and the like. Examples of those compounds are given below.

The hole injecting/transporting material is preferably a material having a high hole mobility to facilitate the injection of holes from an anode and to transport the injected holes to a light emitting layer. Low-molecular and high-molecular materials each having hole injecting/transporting performance are exemplified by, in addition to the indolophenoxazine compound of the present invention, a triarylamine derivative, a phenylenediamine derivative, a stilbene derivative, a phthalocyanine derivative, a porphyrin derivative, poly(vinylcarbazole), poly(thiophene), and other conductive polymers.

The light emitting compound mainly involved in a light emitting function is exemplified by, in addition to the above-mentioned phosphorescent light emitting materials and derivatives thereof, a fused ring compound (for example, a fluorene derivative, a naphthalene derivative, a pyrene derivative, a perylene derivative, a tetracene derivative, an anthracene derivative, or rubrene), a quinacridone derivative, a coumarin derivative, a stilbene derivative, an organic aluminum complex such as tris(8-quinolinolato) aluminum, an organic beryllium complex, and a polymer derivative such as a poly(phenylene vinylene) derivative, a poly(fluorene) derivative, or a poly(phenylene) derivative.

The host included in the light emitting layer is preferably a material having high conductivity for both carriers, i.e., holes and electrons. In addition, a host material for a phosphorescent layer is preferably a material having high $T_1$ energy, and examples thereof include a carbazole derivative, a dibenzofuran derivative, a dibenzothiophene derivative, a fluorene derivative, a phenanthrene derivative, and a triphenylene derivative.

The electron injecting/transporting material may be optionally selected from materials each of which facilitates the injection of electrons from a cathode and is capable of transporting the injected electrons to a light emitting layer, and is selected in consideration of, for example, a balance with the hole mobility of the hole injecting/transporting material. A material having electron injecting/transporting performance is exemplified by an oxadiazole derivative, an oxazole derivative, a pyrazine derivative, a triazole derivative, a triazine derivative, a quinoline derivative, a quinoxaline derivative, a phenanthroline derivative, and an organic aluminum complex.

It is recommended that a material for constructing an anode have as large a work function as possible. For example, metal elements such as gold, platinum, silver, copper, nickel, palladium, cobalt, selenium, vanadium, and tungsten, or alloys including combinations of multiple kinds thereof, and metal oxides such as tin oxide, zinc oxide, indium oxide, indium tin oxide (ITO), and indium zinc oxide may be used. Further, conductive polymers such as polyaniline, polypyrrole, and polythiophene may also be used. One kind of those electrode substances may be used alone, or two or more kinds thereof may be used in combination. Further, the anode may be constructed of a single layer or may be constructed of multiple layers.

Meanwhile, it is recommended that a material for constructing a cathode have a small work function. Examples of the material include alkali metals such as lithium, alkaline earth metals such as calcium, and metal elements such as aluminum, titanium, manganese, silver, lead, and chromium. Alternatively, alloys including combinations of multiple kinds of metal elements described above may also be used. For example, magnesium-silver, aluminum-lithium, aluminum-magnesium, and the like may be used. Metal oxides such as indium tin oxide (ITO) may also be utilized. One kind of those electrode substances may be used alone, or two or more kinds thereof may be used in combination. Further, the cathode may have a single layer construction or may have a multi-layer construction.

In the organic light emitting device of the present invention, a layer including the indolophenoxazine compound of the present invention and other organic compound layers are formed by the following method. In general, a thin film is formed by a vacuum vapor deposition method, an ionization vapor deposition method, a sputtering method, or a plasma method. Alternatively, the thin film may be formed by dissolving the compound in an appropriate solvent and subjecting the resultant to a known coating method (for example, a spin coating method, a dipping method, a casting method, an LB method, or an ink jet method). Here, when the layer is formed by a vacuum vapor deposition method, a solution coating method, or the like, the layer is hard to undergo crystallization and the like and is excellent in stability over time. Further, when the film is formed by a coating method, the film may also be formed in combination with an appropriate binder resin.

Examples of the above-mentioned binder resin include, but not limited to, a poly(vinylcarbazole) resin, a polycarbonate resin, a polyester resin, an ABS resin, an acrylic resin, a polyimide resin, a phenolic resin, an epoxy resin, a silicon resin, and a urea resin. Further, one kind of those binder resins may be used alone as a homopolymer or copolymer, or two or more kinds thereof may be used as a mixture. In addition, a known additive such as a plasticizer, an antioxidant, or an ultraviolet absorber may be used in combination, as necessary.

The organic light emitting device of the present invention may be used for a display apparatus and lighting equipment. In addition, the device may be used for a light source for exposure of an electrophotographic image-forming apparatus, a backlight of a liquid crystal display apparatus, for example.

The display apparatus includes the organic light emitting device according to this embodiment in a display unit. The display unit includes multiple pixels. The pixels each include the organic light emitting device according to this embodiment and a TFT element as one example of a switching element for controlling emission luminance, and an anode or an cathode of the organic light emitting device is connected to a drain electrode or a source electrode of the TFT element. The display apparatus may be used as an image display apparatus such as a PC.

The display apparatus includes an input unit for inputting image information from an area CCD, a linear CCD, a memory card, and the like, and may be an image output device for outputting the input image to a display unit. Further, a display unit included in an image pickup device or an ink jet printer may be provided with both of an image output function, which displays image information input from the outside, and an input function, which serves as an operation panel and inputs processing information for an image. Further, the display apparatus may be used for a display unit of a multifunction printer.

Next, a display apparatus of the present invention is described with reference to the drawings. FIG. 1 is a cross-sectional schematic diagram illustrating an example of a display apparatus including the organic light emitting device of the present invention and a TFT element as one example of a switching element connected to the organic light emitting device. Two sets of the organic light emitting device and the TFT element are illustrated in a display apparatus 20 of FIG. 1. Details of the structure of the display apparatus 20 of FIG. 1 are described below.

The display apparatus 20 of FIG. 1 includes a substrate 1 made of glass or the like and a moisture-proof film 2 for protecting a TFT element or an organic compound layer on the substrate. Further, a gate electrode 3 made of metal is represented by reference numeral 3, a gate insulating film 4 is represented by reference numeral 4, and a semiconductor layer is represented by reference numeral 5.

A TFT element 8 includes the semiconductor layer 5, a drain electrode 6, and a source electrode 7. An insulating film 9 is provided above the TFT element 8. An anode 11 of the organic light emitting device is connected to the source electrode 7 via a contact hole 10. The display apparatus is not limited to the above-mentioned construction, and any one of the anode and a cathode has only to be connected to any one of the source electrode and the drain electrode of the TFT element.

In the display apparatus 20 of FIG. 1, an organic compound layer 12 may include a single organic compound layer or multiple organic compound layers, but is illustrated like a single layer. A first protective layer 14 and a second protective layer 15 for suppressing the deterioration of the organic light emitting device are provided above a cathode 13.

In the display apparatus according to this embodiment, a switching element is not particularly limited, and a monocrystalline silicon substrate, an MIM element, an a-Si type element, or the like may be used.

EXAMPLES

Example 1

Synthesis of Exemplified Compound IP101

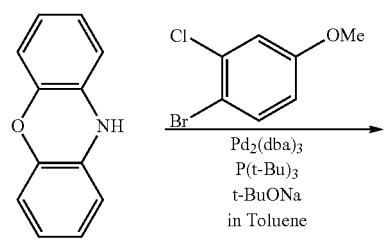

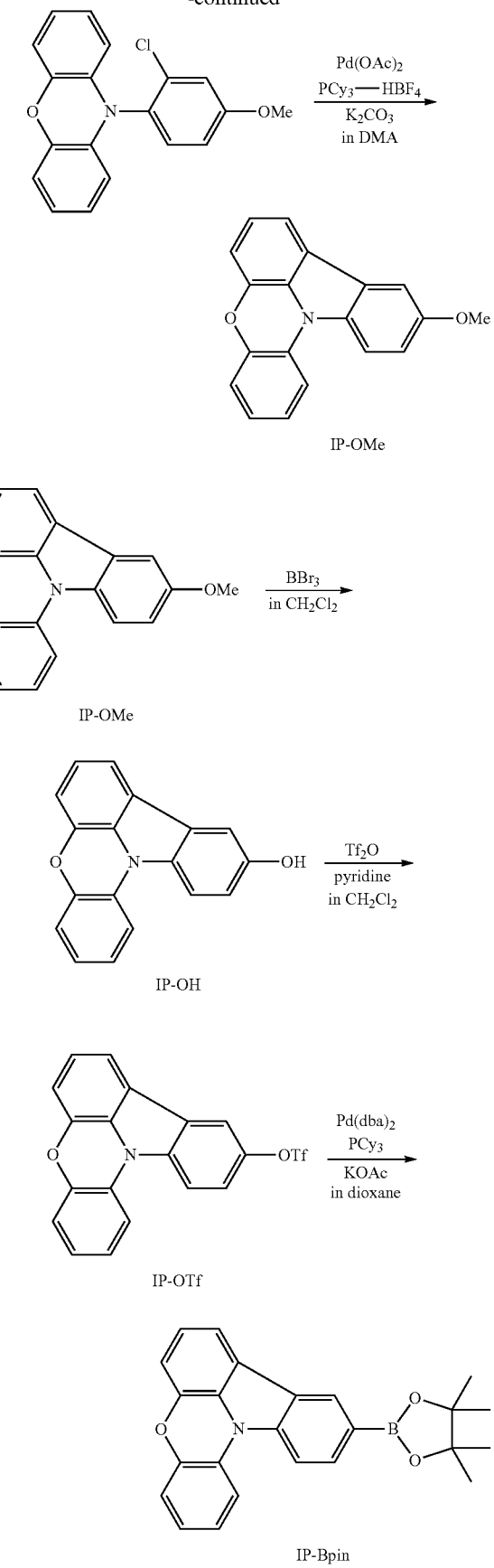

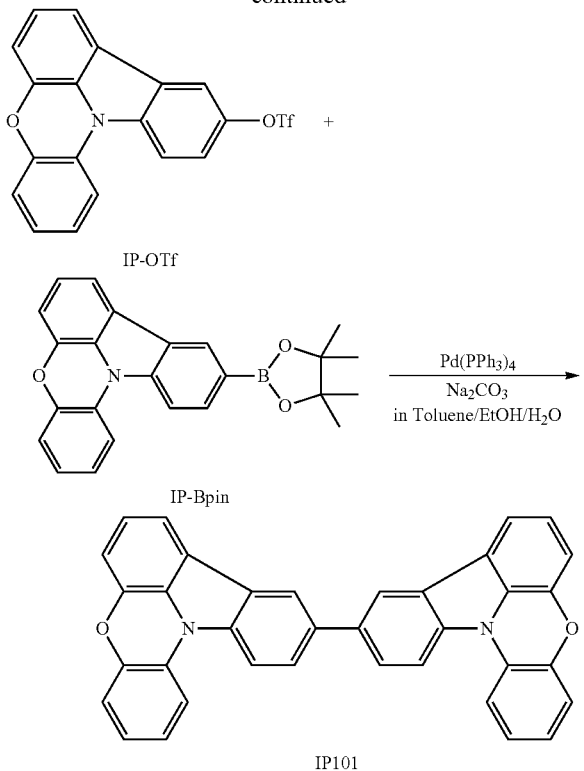

IP-OTf

IP-Bpin

IP101

(1) Synthesis of Intermediate IP-OMe

The following reagents and solvent were loaded into a 300-mL recovery flask.

Phenoxazine: 8.00 g (43.7 mmol)
4-Bromo-3-chloroanisole: 9.21 g (41.6 mmol)
Tris(dibenzylidene)bispalladium: 1.14 g (1.25 mmol)
Tri-tert-butylphosphine: 0.76 g (3.76 mmol)
tert-Butoxysodium: 5.99 g (62.4 mmol)
Toluene: 160 mL Next, the reaction solution was heated at 75° C. for 2 hours with stirring under nitrogen. After the completion of the reaction, the reaction solution was washed with water, dried over sodium sulfate, and then concentrated under reduced pressure to give a crude product. Next, the resultant crude product was purified by silica gel column chromatography (eluent: heptane/toluene=4/1) to afford 7.60 g of 10-(2-chloro-4-methoxyphenyl)phenoxazine (yield: 57%).

Subsequently, the following reagents were loaded into a 300-mL recovery flask, and gas in the recovery flask was replaced by nitrogen.

10-(2-Chloro-4-methoxyphenyl)phenoxazine: 7.60 g (23.5 mmol)
Palladium acetate: 317 mg (1.41 mmol)
Tricyclohexylphosphonium tetrafluoroborate: 1.04 g (2.82 mmol)
Potassium carbonate: 6.49 g (46.9 mmol)

Next, 150 mL of N,N-dimethylacetamide, into which nitrogen had been bubbled, were added. The reaction solution was then heated at 135° C. for 6 hours with stirring under nitrogen. After the completion of the reaction, the reaction solution was filtered by short silica gel column chromatography (eluent: heptane/ethyl acetate=10/1). The filtrate was then concentrated under reduced pressure to give a crude product. Next, the resultant crude product was purified by silica gel column chromatography (eluent: heptane/toluene=2/1) to afford 6.16 g of an intermediate IP-OMe (yield: 91%).

Further, the resultant compound was identified by $^1$H-NMR measurement.

[$^1$H-NMR (400 MHz, CDCl$_3$)] δ 7.77 (d, 1H), 7.56 (dd, 1H), 7.48 (d, 1H), 7.38 (d, 1H), 7.13 (dd, 1H), 7.05-6.90 (m, 4H), 6.68 (d, 1H), 3.93 (s, 3H).

(2) Synthesis of Intermediate IP-Bpin

The following reagent and solvent were loaded into a 300-mL recovery flask.

IP-OMe: 6.13 g (21.3 mmol)
Dry dichloromethane: 200 mL

Next, the reaction solution was cooled to 0° C. with stirring under nitrogen. After that, 25.7 mL (25.7 mmol) of BBr$_3$ (1M solution in dichloromethane) were added dropwise through a dropping funnel to the reaction solution over 20 minutes. After the completion of the dropwise addition, the reaction solution was warmed to room temperature and stirred at the same temperature (room temperature) for additional 3 hours. The reaction was then quenched by the addition of methanol. Next, the reaction solution was concentrated under reduced pressure. Ethanol was then added to the residue to produce a precipitate. The precipitate was collected by filtration to give a crude product. The resultant crude product was further purified by recrystallization from an ethyl acetate/heptane solvent to afford 5.39 g of an intermediate IP-OH (yield: 92%).

Subsequently, the following reagents and solvent were loaded into a 300-mL recovery flask.

IP-OH: 3.00 g (11.0 mmol)
Pyridine: 1.74 g (22.0 mmol)
Dry dichloromethane: 200 mL Next, the reaction solution was cooled to 0° C. with stirring under nitrogen. After that, a solution, which was prepared by mixing 2.40 mL (14.3 mmol) of trifluoromethanesulfonic anhydride with 20 mL of dichloromethane, was added dropwise through a dropping funnel to the reaction solution over 20 minutes. After the completion of the dropwise addition, the mixture was continuously stirred at 0° C. for additional 1 hour. The reaction was then quenched by the addition of water. Subsequently, chloroform was added to the reaction solution, and orange insoluble matter was then removed by filtration. Next, the filtrate was washed with water, dried over sodium sulfate, and then concentrated under reduced pressure to give a crude product. Next, the resultant crude product was purified by silica gel column chromatography (eluent: heptane/toluene=1/1) to afford 2.57 g of an intermediate IP-OTf (yield: 58%).

Subsequently, the following reagents and solvent were loaded into a 200-mL recovery flask.

IP-OTf: 2.57 g (6.35 mmol)
Bis(pinacolato)diboron: 2.42 g (6.35 mmol)
Bis(dibenzylideneacetone)palladium(0): 183 mg (0.32 mmol)
Tricyclohexylphosphine: 267 mg (0.95 mmol)
Potassium acetate: 1.87 g (19.1 mmol)
1,4-Dioxane: 100 mL The reaction solution was heated at 95° C. for 5 hours with stirring under nitrogen. After the completion of the reaction, the reaction solution was washed with water, dried over sodium sulfate, and then concentrated under reduced pressure to give a crude product. Next, the resultant crude product was purified by silica gel column chromatography (eluent: heptane/toluene=1/2) to afford 1.80 g of an intermediate IP-Bpin (yield: 74%).

(3) Synthesis of Exemplified Compound IP101

The following reagents and solvents were loaded into a 50-mL recovery flask.
IP-OTf: 400 mg (0.987 mmol)
IP-Bpin: 397 mg (1.04 mmol)
Tetrakis(triphenylphosphine)palladium(0): 34 mg (30 μmol)
Toluene: 12 mL
Ethanol: 6 mL
10-wt % aqueous solution of sodium carbonate: 6 mL Next, the reaction solution was refluxed with heating for 4 hours with stirring under nitrogen. After the completion of the reaction, water was added to the reaction solution, the mixture was stirred, and the precipitated crystal was separated by filtration. The crystal was then successively washed with water, ethanol, and acetone to give a crude product. Next, the resultant crude product was dissolved with heating in chlorobenzene and then subjected hot filtration, followed by recrystallization from a chlorobenzene solvent. The resultant crystal was dried in vacuo at 150° C. and then subjected to sublimation purification under the conditions of $1\times10^{-4}$ Pa and 390° C. to afford 233 mg of Exemplified Compound IP101 with a high purity (yield: 46%).

The resultant compound was identified by mass spectrometry.

[Matrix-assisted laser desorption/ionization time-of-flight mass spectrometry (MALDI-TOF-MS)]

Observed value: m/z=512.32, calculated value: $C_{36}H_{20}N_2O_2$=512.15.

Further, Exemplified Compound IP101 was measured for its $T_1$ energy by the following method.

A toluene dilute solution of Exemplified Compound IP101 was measured for its phosphorescence spectrum at an excitation wavelength of 350 nm under an Ar atmosphere at 77 K. The $T_1$ energy was determined from the peak wavelength of the first emission peak in the resultant phosphorescence spectrum, and found to be 485 nm in terms of a wavelength.

Next, Exemplified Compound IP101 was measured for its ionization potential by the following method.

Exemplified Compound IP101 was formed into a vapor deposition thin film having a thickness of 20 nm on glass substrate by heating vapor deposition. The vapor deposition thin film was measured for its ionization potential with a photoelectron spectrometer AC-3 (manufactured by RIKEN KEIKI CO., LTD.). As a result of the measurement, Exemplified Compound IP101 had an ionization potential of 5.59 eV.

Example 2

Synthesis of Exemplified Compound IP201

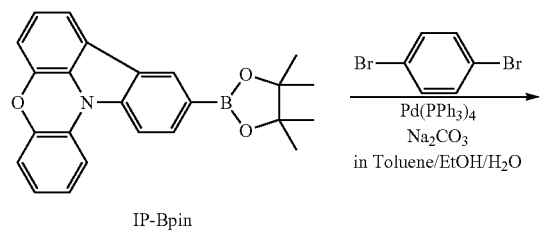

IP-Bpin

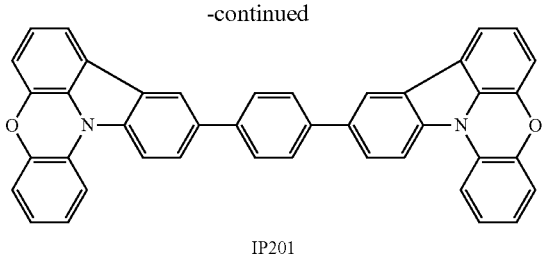

IP201

The following reagents and solvents were loaded into a 200-mL recovery flask.
1,4-Dibromobenzene: 358 mg (1.52 mmol)
IP-Bpin: 1.22 g (3.19 mmol)
Tetrakis(triphenylphosphine)palladium(0): 88 mg (76 μmol)
Toluene: 30 mL
Ethanol: 15 mL
10-wt % aqueous solution of sodium carbonate: 15 mL Next, the reaction solution was refluxed with heating for 3 hours with stirring under nitrogen. After the completion of the reaction, water was added to the reaction solution, the mixture was stirred, and the precipitated crystal was separated by filtration. Next, the crystal was successively washed with water, ethanol, and acetone to give a crude product. Next, the resultant crude product was dissolved with heating in o-dichlorobenzene and then subjected to hot filtration, followed by recrystallization from an o-dichlorobenzene solvent. Next, the resultant crystal was dried in vacuo at 150° C. and then subjected to sublimation purification under the conditions of $1\times10^{-4}$ Pa and 410° C. to afford 264 mg of Exemplified Compound IP201 with a high purity (yield: 30%).

The resultant compound was identified by mass spectrometry.

[MALDI-TOF-MS]
Observed value: m/z=588.28, calculated value: $C_{42}H_{24}N_2O_2$=588.18.

Further, the $T_1$ energy of Exemplified Compound IP201 was measured by the same method as in Example 1, and found to be 477 nm in terms of a wavelength.

In addition, the ionization potential of Exemplified Compound IP201 was measured by the same method as in Example 1. As a result, Exemplified Compound IP201 was found to have an ionization potential of 5.67 eV.

Example 3

Synthesis of Exemplified Compound IP202

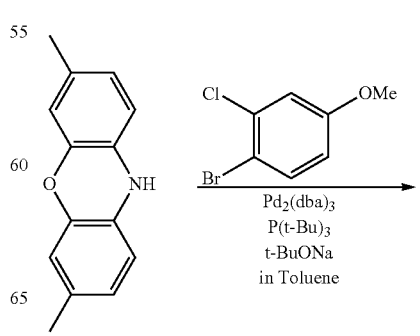

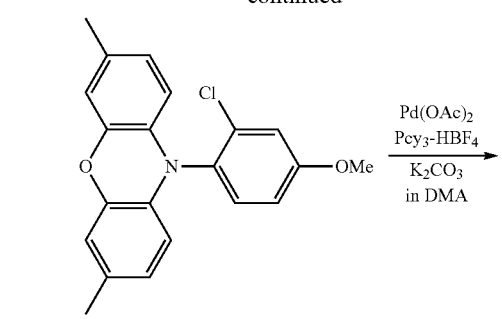

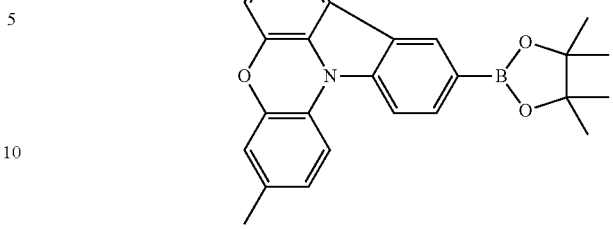

DMIP-Bpin

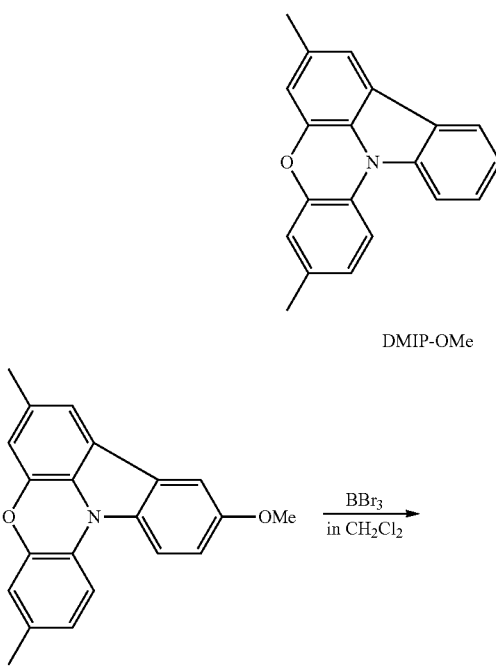

DMIP-OMe

DMIP-OMe

DMIP-OH

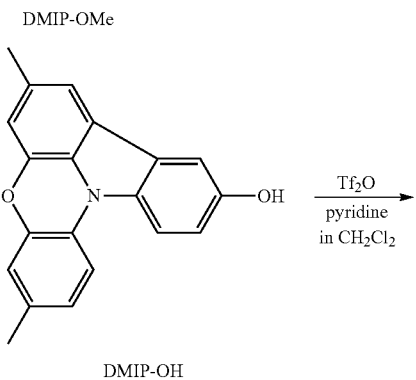

DMIP-Bpin

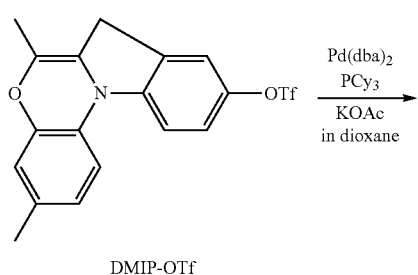

IP202

DMIP-OTf (1) Synthesis of DMIP-Bpin

An intermediate 3,7-dimethyl-10-(4,4,5,5-tetramethyl-1,3,2-dioxaborolan-2-yl)indolophenoxazine (DMIP-Bpin) was synthesized by the same method as in Example 1 (1) and (2) except that 3,7-dimethylphenoxazine was used in place of phenoxazine in Example 1(1).

(2) Synthesis of Exemplified Compound IP202

The following reagents and solvents were loaded into a 50-mL recovery flask.

1,4-Dibromobenzene: 137 mg (0.581 mol)
DMIP-Bpin: 500 mg (1.22 mmol)
Tetrakis(triphenylphosphine)palladium(0): 33 mg (29 μmol)
Toluene: 12 mL
Ethanol: 6 mL
10-wt % aqueous solution of sodium carbonate: 6 mL Next, the reaction solution was refluxed with heating for 5 hours with stirring under nitrogen. After the completion of the reaction, water was added to the reaction solution, the mixture was stirred, and the precipitated crystal was separated by filtration. The crystal was then successively washed with water, ethanol, and acetone to give a crude product. Next, the resultant crude product was dissolved with heating in chlorobenzene and then subjected to hot filtration, followed by recrystallization from a chlorobenzene solvent. Next, the resultant crystal was dried in vacuo at 150° C. and then subjected to sublimation purification under the conditions of $1\times10^{-4}$ Pa and 405° C. to afford 165 mg of Exemplified Compound IP202 with a high purity (yield: 44%).

The resultant compound was identified by mass spectrometry.

[MALDI-TOF-MS]

Observed value: m/z=644.36, calculated value: $C_{46}H_{32}N_2O_2$=644.25.

Further, the $T_1$ energy of Exemplified Compound IP202 was measured by the same method as in Example 1, and found to be 478 nm in terms of a wavelength.

In addition, the ionization potential of Exemplified Compound IP202 was measured by the same method as in Example 1. As a result, Exemplified Compound IP202 was found to have an ionization potential of 5.53 eV.

Example 4

Synthesis of Exemplified Compound IP301

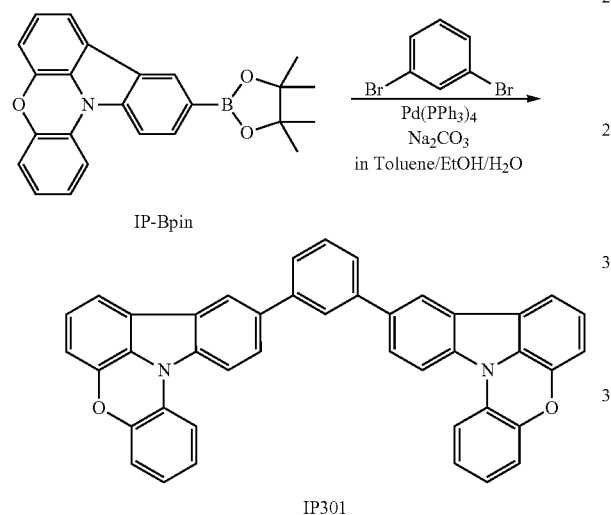

The following reagents and solvents were loaded into a 100-mL recovery flask.

1,3-Dibromobenzene: 293 mg (1.24 mmol)

IP-Bpin: 1.00 g (2.61 mmol)

Tetrakis(triphenylphosphine)palladium(0): 72 mg (62 μmol)

Toluene: 20 mL

Ethanol: 10 mL 10-wt % aqueous solution of sodium carbonate: 10 mL

Next, the reaction solution was refluxed with heating for 6 hours with stirring under nitrogen. After the completion of the reaction, water was added to the reaction solution, the mixture was stirred, and the precipitated crystal was separated by filtration. The crystal was then successively washed with water, ethanol, and acetone to give a crude product. Next, the resultant crude product was dissolved with heating in chlorobenzene and then subjected to hot filtration, followed by recrystallization from a chlorobenzene solvent. Next, the resultant crystal was dried in vacuo at 150° C. and then subjected to sublimation purification under the conditions of 1×10$^{-4}$ Pa and 380° C. to afford 585 mg of Exemplified Compound IP301 with a high purity (yield: 38%).

The resultant compound was identified by mass spectrometry.

[MALDI-TOF-MS]

Observed value: m/z=587.97, calculated value: $C_{42}H_{24}N_2O_2$=588.18.

Further, the $T_2$ energy of Exemplified Compound IP301 was measured by the same method as in Example 1, and found to be 448 nm in terms of a wavelength.

In addition, the ionization potential of Exemplified Compound IP301 was measured by the same method as in Example 1. As a result, Exemplified Compound IP301 was found to have an ionization potential of 5.76 eV.

Comparative Examples 1 to 4

Comparisons for $T_1$ Energy and Ionization Potential

Comparative Compounds H01 to H04 shown below were each measured for its $T_1$ energy and ionization potential by the same method as in Example 1. Table 4 shows the results together with the results of Examples 1 to 4.

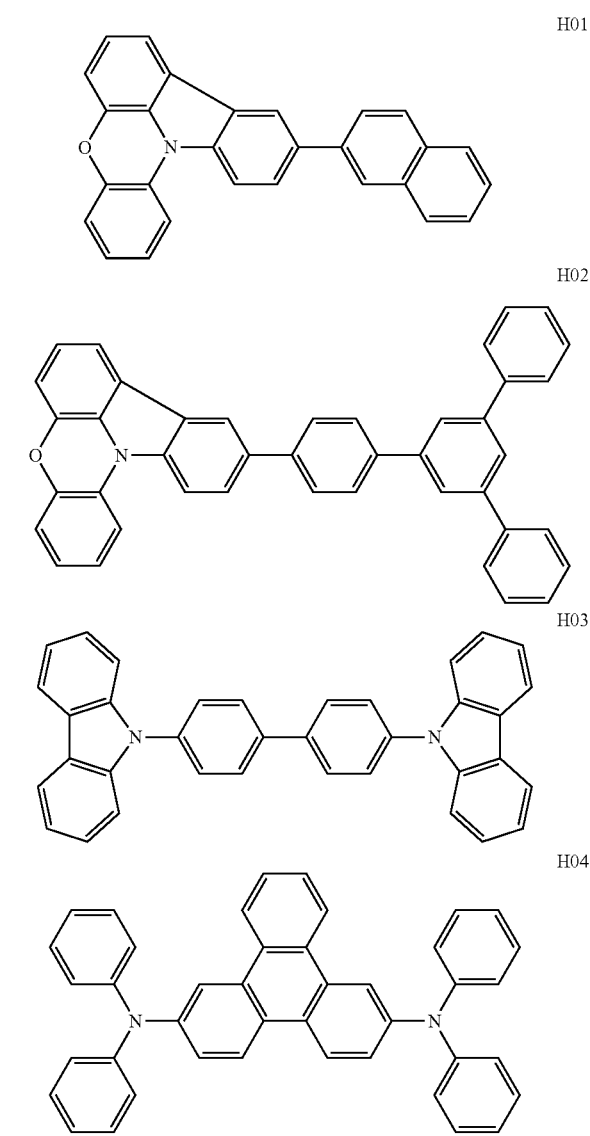

TABLE 4

| | Compound | T₁ (Note 1) [nm] | Ionization potential [eV] |
|---|---|---|---|
| Example 1 | IP101 | 485 | 5.59 |
| Example 2 | IP201 | 477 | 5.67 |
| Example 3 | IP202 | 478 | 5.53 |
| Example 4 | IP301 | 448 | 5.76 |
| Comparative Example 1 | H01 | 499 | 5.86 |
| Comparative Example 2 | H02 | 475 | 5.80 |
| Comparative Example 3 | H03 | 464 | 6.20 |
| Comparative Example 4 | H04 | 501 | 5.55 |

(Note 1) In terms of wavelength

Table 4 showed that the compounds synthesized in Examples 1 to 4 each had high $T_1$ energy and a small ionization potential (shallow HOMO level) as compared to the comparative compounds (H01 to H04).

Here, the compounds synthesized in Examples 1 to 4 each have higher $T_1$ energy than that of Comparative Compound H01. The difference corresponds to a difference in $T_1$ energy between aryl substituents to each of which the indolophenoxazine ring is bonded. That is, in the exemplified compounds, the aryl substituent to which the indolophenoxazine ring is bonded is a substituent having $T_1$ energy equal to or higher than that of indolophenoxazine, i.e., an indolophenoxazyl group or an oligophenylene group. Thus, a reduction in $T_1$ energy due to extended π-conjugation becomes small in the compound as a whole.

Further, the compounds synthesized in Examples 1 to 4 each have higher $T_1$ energy than that of Comparative Compound H04. The difference results from an indolophenoxazine ring having high $T_1$ energy, suggesting that the indolophenoxazine compound of the present invention has higher $T_1$ energy than that of an aryldiamine compound as a general hole transporting material.

Further, the compounds synthesized in Examples 1 to 4 each have a smaller ionization potential than those of the Comparative Compounds H01 and H02. This suggests that the compounds synthesized in Examples 1 to 4 each have two indolophenoxazine rings in a molecule, and hence have a small ionization potential.

In addition, the compounds synthesized in Examples 1 to 4 each have a smaller ionization potential than that of Comparative Compound H03. The difference corresponds to a difference in HOMO level between main skeletons in molecules. That is, this suggests that an indolophenoxazine skeleton has a shallower HOMO level than that of a carbazole skeleton, and hence the compound as a whole also has a shallow HOMO level.

Example 5

In this example, an organic light emitting device having the construction of "anode/hole transport layer/light emitting layer/hole blocking layer/electron transport layer/cathode" successively provided on a substrate was produced by the following method. It should be noted that some of compounds used in this example are shown below.

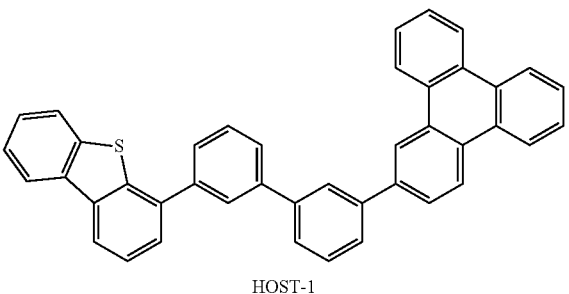

HOST-1

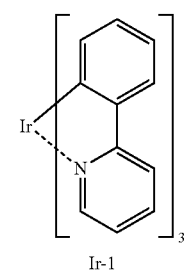

Ir-1

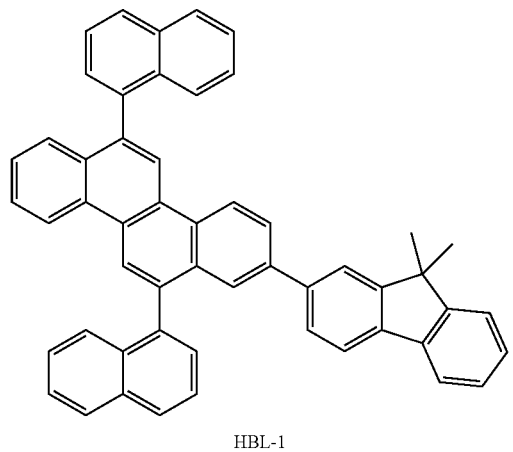

HBL-1

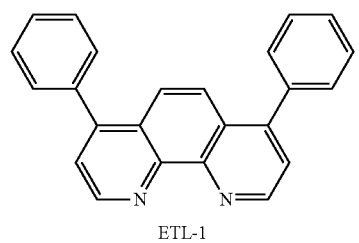

ETL-1

First, ITO was formed into a film to serve as an anode on a glass substrate by a sputtering method. In this case, the thickness of the anode was set to 120 nm. The substrate having provided thereon the ITO electrode (anode) as described above was used as a transparent conductive supporting substrate (ITO substrate) in the following steps. Next, organic compound layers and electrode layers shown in Table 5 below were continuously formed as films on the ITO substrate by vacuum vapor deposition through resistance heating in a vacuum chamber at $1\times10^{-5}$ Pa. In this case, an opposite electrode (cathode) was produced so as to have an area of 3 mm².

TABLE 5

| | Material | Thickness [nm] |
|---|---|---|
| Hole transport layer | Exemplified Compound IP101 | 40 |
| Light emitting layer | Host: HOST-1 Guest: Ir-1 (host:guest=90:10 (weight ratio)) | 30 |
| Hole blocking layer | HBL-1 | 10 |
| Electron transport layer | ETL-1 | 30 |
| First metal electrode layer (cathode) | LiF | 0.5 |
| Second metal electrode layer (cathode) | Al | 100 |

Next, the resultant was covered with a protective glass sheet and sealed with an acrylic resin-based adhesive under a dry air atmosphere in order that an organic light emitting device did not undergo device deterioration due to moisture adsorption. Thus, an organic light emitting device was obtained.

A voltage of 5.0 V was applied to the resultant organic light emitting device while the ITO electrode was used as a positive electrode and the Al electrode was used as a negative electrode. As a result, the device was observed to emit green light having an emission efficiency of 46.0 cd/A and a luminance of 2,500 cd/m$^2$. Further, the device had CIE chromaticity coordinates of (x, y)=(0.33, 0.62). In addition, the light emitting device showed a luminance half-life of 108 hours at a constant current density of 100 mA/cm$^2$.

Example 6

An organic light emitting device was produced by the same method as in Example 5 except that Exemplified Compound IP105 was used in place of Exemplified Compound IP101 as the material for constructing the hole transport layer in Example 5. Further, the resultant device was evaluated in the same manner as in Example 5. Table 6 shows the results.

Example 7

An organic light emitting device was produced by the same method as in Example 5 except that Exemplified Compound IP201 was used in place of Exemplified Compound IP101 as the material for constructing the hole transport layer in Example 5. Further, the resultant device was evaluated in the same manner as in Example 5. Table 6 shows the results.

Example 8

An organic light emitting device was produced by the same method as in Example 5 except that Exemplified Compound IP202 was used in place of Exemplified Compound IP101 as the material for constructing the hole transport layer in Example 5. Further, the resultant device was evaluated in the same manner as in Example 5. Table 6 shows the results.

Example 9

An organic light emitting device was produced by the same method as in Example 5 except that Exemplified Compound IP301 was used in place of Exemplified Compound IP101 as the material for constructing the hole transport layer in Example 5. Further, the resultant device was evaluated in the same manner as in Example 5. Table 6 shows the results.

Example 10

An organic light emitting device was produced by the same method as in Example 5 except that Exemplified Compound 401 was used in place of Exemplified Compound IP101 as the material for constructing the hole transport layer in Example 5. Further, the resultant device was evaluated in the same manner as in Example 5. Table 6 shows the results.

Example 11

An organic light emitting device was produced by the same method as in Example 5 except that Exemplified Compound IP502 was used in place of Exemplified Compound IP101 as the material for constructing the hole transport layer in Example 5. Further, the resultant device was evaluated in the same manner as in Example 5. Table 6 shows the results.

Comparative Example 5

An organic light emitting device was produced by the same method as in Example 5 except that Comparative Compound H03 was used in place of Exemplified Compound IP101 as the material for constructing the hole transport layer in Example 5. Further, the resultant device was evaluated in the same manner as in Example 5. Table 6 shows the results.

Comparative Example 6

An organic light emitting device was produced by the same method as in Example 5 except that Comparative Compound H04 was used in place of Exemplified Compound IP101 as the material for constructing the hole transport layer in Example 5. Further, the resultant device was evaluated in the same manner as in Example 5. Table 6 shows the results.

TABLE 6

| | Hole transport layer | CIE chromaticity coordinates | At 2,500 cd/m$^2$ | | Luminance half-life at 100 mA/cm$^2$ (hr) |
|---|---|---|---|---|---|
| | | | Applied voltage (V) | Emission efficiency (cd/A) | |
| Example 5 | IP101 | (0.33, 0.62) | 5.0 | 46.0 | 108 |
| Example 6 | IP105 | (0.32, 0.62) | 4.9 | 45.5 | 91 |
| Example 7 | IP201 | (0.32, 0.62) | 5.1 | 46.5 | 120 |
| Example 8 | IP202 | (0.33, 0.64) | 4.7 | 47.9 | 96 |
| Example 9 | IP301 | (0.32, 0.63) | 5.3 | 51.1 | 117 |
| Example 10 | IP401 | (0.32, 0.62) | 5.2 | 49.3 | 85 |
| Example 11 | IP502 | (0.32, 0.63) | 5.4 | 50.6 | 110 |
| Comparative Example 5 | H03 | (0.30, 0.64) | 6.5 | 45.1 | 38 |
| Comparative Example 6 | H04 | (0.31, 0.63) | 4.8 | 38.3 | 72 |

As described above, the indolophenoxazine compound of the present invention is a compound characterized by having high chemical stability, high $T_1$ energy, and a shallow HOMO level. Thus, the use of the compound as a material for constructing a hole transport layer included in an organic light emitting device provides an organic light emitting device having high emission efficiency and a long life.

Example 12

In this example, an organic light emitting device having the construction of "anode/first hole transport layer/second hole transport layer/light emitting layer/electron transport layer/cathode" successively provided on a substrate was produced by the following method. It should be noted that the first hole transport layer and the second hole transport layer are hole transport layers having ionization potentials different from each other. Further, some of compounds used in this example are shown below.

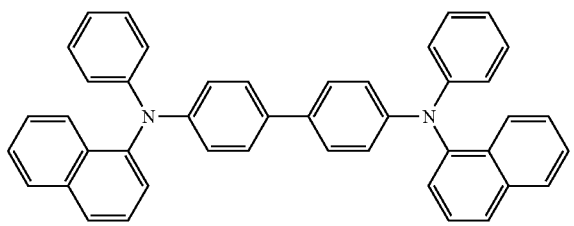

HTL-1

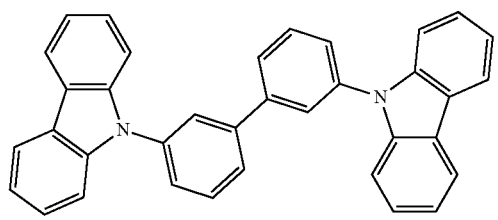

HOST-2

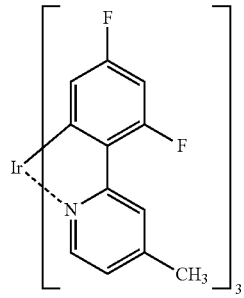

Ir-13

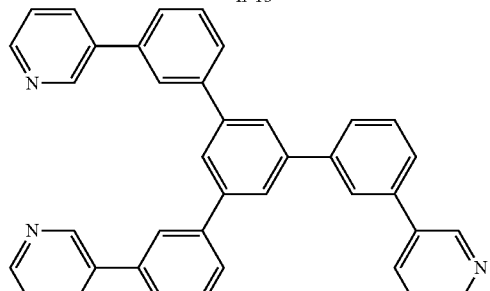

ETL-2

First, an ITO substrate was produced by the same method as in Example 5. Next, organic compound layers and electrode layers shown in Table 7 below were continuously formed as films on the ITO substrate by vacuum vapor deposition through resistance heating in a vacuum chamber at $1 \times 10^{-5}$ Pa. In this case, an opposite electrode (cathode) was produced so as to have an area of 3 mm$^2$.

TABLE 7

| | Material | Thickness [nm] |
|---|---|---|
| First hole transport layer | HTL-1 | 30 |
| Second hole transport layer | Exemplified Compound IP301 | 20 |
| Light emitting layer | Host: HOST-2 Guest: Ir-13 (host:guest=90:10 (weight ratio)) | 40 |
| Electron transport layer | ETL-2 | 30 |
| First metal electrode layer (cathode) | LiF | 0.5 |
| Second metal electrode layer (cathode) | Al | 100 |

Next, the resultant was covered with a protective glass sheet and sealed with an acrylic resin-based adhesive under a dry air atmosphere so that an organic light emitting device did not undergo device deterioration due to moisture adsorption. Thus, an organic light emitting device was obtained.

A voltage of 5.3 V was applied to the resultant organic light emitting device while the ITO electrode was used as a positive electrode and the Al electrode was used as a negative electrode. As a result, the device was observed to emit blue light having an emission efficiency of 17.4 cd/A and a luminance of 2,000 cd/m$^2$. Further, the device had CIE chromaticity coordinates of (x, y)=(0.17, 0.35). In addition, the light emitting device showed a luminance half-life of 130 hours at a constant current density of 4 mA/cm$^2$.

Example 13

An organic light emitting device was produced by the same method as in Example 12 except that Exemplified Compound IP302 was used in place of Exemplified Compound IP301 as the material for constructing the second hole transport layer in Example 12. Further, the resultant device was evaluated in the same manner as in Example 12. Table 8 shows the results.

Example 14

An organic light emitting device was produced by the same method as in Example 12 except that Exemplified Compound IP502 was used in place of Exemplified Compound IP301 as the material for constructing the second hole transport layer in Example 12. Further, the resultant device was evaluated in the same manner as in Example 12. Table 8 shows the results.

Comparative Example 7

An organic light emitting device was produced by the same method as in Example 12 except that Comparative Compound H04 was used in place of Exemplified Compound IP301 as the material for constructing the second hole transport layer in Example 12. Further, the resultant device was evaluated in the same manner as in Example 12. Table 8 shows the results.

TABLE 8

| | Hole transport layer 2 | CIE chromaticity coordinates | At 2,000 cd/m² Applied voltage (V) | At 2,000 cd/m² Emission efficiency (cd/A) | Luminance half-life at 4 mA/cm² (hr) |
|---|---|---|---|---|---|
| Example 12 | IP301 | (0.17, 0.35) | 5.3 | 17.4 | 130 |
| Example 13 | IP302 | (0.17, 0.35) | 5.2 | 16.2 | 106 |
| Example 14 | IP502 | (0.18, 0.36) | 5.4 | 17.9 | 90 |
| Comparative Example 7 | H04 | (0.18, 0.37) | 5.0 | 8.5 | 66 |

As described above, the indolophenoxazine compound of the present invention is a compound characterized by having high chemical stability, high $T_1$ energy, and a shallow HOMO level. Thus, the use of the compound as a material for constructing, in particular, a hole transport layer in an organic light emitting device can provide a light emitting device having high emission efficiency and a long life.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-275736, filed Dec. 10, 2010, which is hereby incorporated by reference herein in its entirety.

REFERENCE SIGNS LIST 1 substrate
2 moisture-proof film
3 gate electrode
4 gate insulating film
5 semiconductor layer
6 drain electrode
7 source electrode
8 TFT element
9 insulating film
10 contact hole
11 anode
12 organic compound layer
13 cathode
14 first protective layer
15 second protective layer
20 display apparatus

The invention claimed is:

1. An indolophenoxazine compound, which is represented by the following general formula [1]:

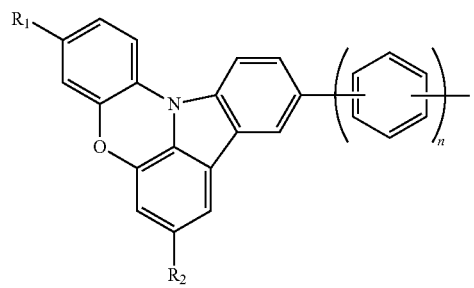

[1]

-continued

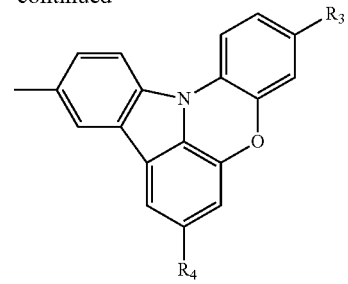

in the formula [1], $R_1$ to $R_4$ each represents one of a hydrogen atom and an alkyl group having 1 to 4 carbon atoms, and n represents an integer of 1 to 3.

2. The indolophenoxazine compound according to claim 1, wherein each of $R_1$ to $R_4$ represents a hydrogen atom.

3. The indolophenoxazine compound according to claim 2, wherein the indolophenoxazine compound comprises a compound represented by the following general formula [2]:

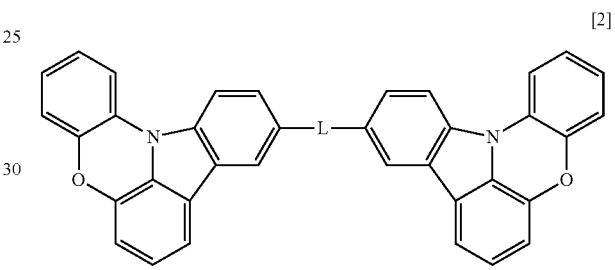

[2]

in the formula [2], L is selected from the group consisting of an m-phenylene group and a p-phenylene group.

4. An organic light emitting device comprising:
an anode;
a cathode; and
an organic compound layer disposed between the anode and the cathode,
wherein the organic compound layer comprises the indolophenoxazine compound according to claim 1.

5. The organic light emitting device according to claim 4, wherein the indolophenoxazine compound is contained in one of a hole injection layer and a hole transport layer.

6. The organic light emitting device according to claim 5, wherein the organic compound layer comprises a light emitting layer; and
wherein the light emitting layer comprises a phosphorescent light emitting material.

7. The organic light emitting device according to claim 6, wherein the phosphorescent light emitting material comprises an iridium complex.

8. A display apparatus comprising:
the organic light emitting device according to claim 4; and
a switching element connected to the organic light emitting device.

9. A lighting equipment comprising the organic light emitting device according to claim 4.

10. The indolophenoxazine compound according to claim 1, wherein an oligophenylene in the general formula [1] is bonded to each indolophenoxazine backbone at meta position.

11. An indolophenoxazine compound, which is represented by the following general formula [1]:

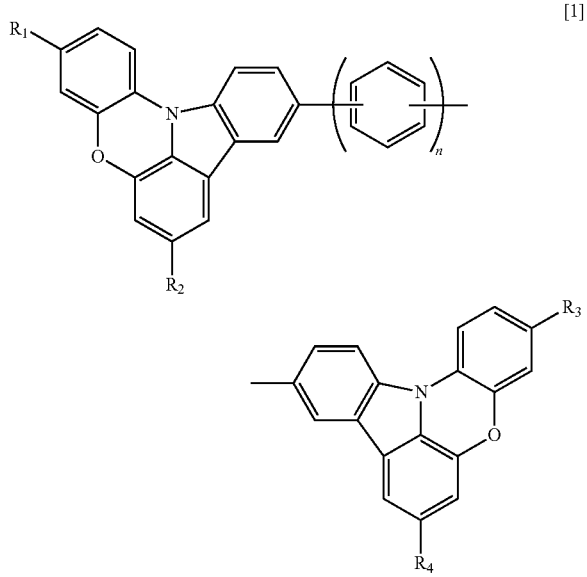

in the formula [1], $R_1$ to $R_4$ each represents one of a hydrogen atom and an alkyl group having 1 to 4 carbon atoms, and n represents an integer of 0 to 3,
wherein at least one of $R_1$ to $R_4$ represents an alkyl group having 1 to 4 carbon atoms.

12. The indolophenoxazine compound according to claim 11, wherein the n represents an integer of 1 to 3; and
wherein the oligophenylene in the general formula [1] is bonded to each indolophenoxazine backbone at meta position.

13. An organic light emitting device comprising:
an anode;
a cathode; and
an organic compound layer disposed between the anode and the cathode,
wherein the organic compound layer comprises the indolophenoxazine compound according to claim 11.

14. The organic light emitting device according to claim 13, wherein the indolophenoxazine compound is contained in at least one of a hole injection layer and a hole transport layer.

15. The organic light emitting device according to claim 13, wherein the organic compound layer comprises a light emitting layer; and
wherein the light emitting layer comprises a phosphorescent light emitting material.

16. A display apparatus comprising:
the organic light emitting device according to claim 13; and
a switching element connected to the organic light emitting device.

17. A lighting equipment comprising the organic light emitting device according to claim 13.

* * * * *